(12) United States Patent
Börtlein et al.

(10) Patent No.: US 9,662,206 B2
(45) Date of Patent: May 30, 2017

(54) TRANSCATHETER VALVE PROSTHESIS

(75) Inventors: Georg Börtlein, Paris (FR); Malek Nasr, Paris (FR)

(73) Assignee: HIGHLIFE SAS, Paris (FR)

( * ) Notice: Subject to any disclaimer, the term of this patent is extended or adjusted under 35 U.S.C. 154(b) by 241 days.

(21) Appl. No.: 14/342,237

(22) PCT Filed: Jun. 13, 2012

(86) PCT No.: PCT/EP2012/061237
§ 371 (c)(1),
(2), (4) Date: Mar. 11, 2014

(87) PCT Pub. No.: WO2013/037519
PCT Pub. Date: Mar. 21, 2013

(65) Prior Publication Data
US 2014/0214157 A1    Jul. 31, 2014

Related U.S. Application Data

(60) Provisional application No. 61/543,331, filed on Oct. 5, 2011.

(30) Foreign Application Priority Data

Sep. 12, 2011   (DE) .................. 10 2011 053 520
Oct. 4, 2011    (DE) .................. 10 2011 054 172

(51) Int. Cl.
*A61F 2/24*     (2006.01)
*A61F 2/848*    (2013.01)

(52) U.S. Cl.
CPC .............. *A61F 2/2427* (2013.01); *A61F 2/24* (2013.01); *A61F 2/243* (2013.01); *A61F 2/2418* (2013.01);
(Continued)

(58) Field of Classification Search
CPC ........ A61F 2/24; A61F 2/2412; A61F 2/2403; A61F 2/2424; A61F 2/91; A61F 2/2418;
(Continued)

(56) References Cited

U.S. PATENT DOCUMENTS 8,236,049 B2    8/2012    Rowe et al.
8,323,335 B2    12/2012   Rowe et al.
(Continued)

FOREIGN PATENT DOCUMENTS

DE    102005052628 A1    5/2007
DE    10 2011 054 172 A1    3/2013
(Continued)

OTHER PUBLICATIONS

Aug. 11, 2014 Office Action issued in U.S. Appl. No. 14/204,518.
(Continued)

*Primary Examiner* — Thomas J Sweet
*Assistant Examiner* — Seema Mathew
(74) *Attorney, Agent, or Firm* — Oliff PLC

(57) ABSTRACT

A transcatheter atrio-ventricular valve prosthesis for functional replacement of an atrio-ventricular heart valve in a connection channel, the prosthesis comprising a radially expandable tubular body extending along an axis, and a valve arranged within and attached to the tubular body. The tubular body is provided with an outer circumferential groove which is open to the radial outside of the tubular body, whereby the tubular body is separated by the outer circumferential groove into first and second body sections. The tubular body is provided with a first plurality of projections which extend from the first or second body section in an axial direction of the tubular body and each of which has a free end arranged to overlap the outer circumferential
(Continued)

groove. An elongate outer member may be disposed at the exterior of the connection channel wall structure at a level of the circumferential groove.

10 Claims, 12 Drawing Sheets

(52) U.S. Cl.
CPC ............... *A61F 2002/8483* (2013.01); *A61F 2220/0008* (2013.01); *A61F 2220/0016* (2013.01); *A61F 2230/008* (2013.01); *A61F 2230/0054* (2013.01); *A61F 2230/0078* (2013.01); *A61F 2250/006* (2013.01); *A61F 2250/0069* (2013.01)

(58) Field of Classification Search
CPC ............ A61F 2/2409; A61F 2002/249; A61F 2210/0014; A61F 2220/0008; A61F 2250/006; A61F 2250/0063; A61F 2/2427; A61F 2/2445; A61F 2/246
See application file for complete search history.

(56) References Cited

U.S. PATENT DOCUMENTS

| | | | |
|---|---|---|---|
| 8,398,708 B2 | 3/2013 | Meiri et al. | |
| 8,449,605 B2 | 5/2013 | Lichtenstein et al. | |
| 8,597,348 B2 | 12/2013 | Rowe et al. | |
| 8,623,079 B2* | 1/2014 | Savage | A61F 2/2418 623/1.26 |
| 9,375,312 B2 | 6/2016 | Weber | |
| 2005/0137686 A1* | 6/2005 | Salahieh | A61F 2/2418 623/2.11 |
| 2005/0182486 A1 | 8/2005 | Gabbay | |
| 2006/0058872 A1 | 3/2006 | Salahieh et al. | |
| 2006/0135967 A1* | 6/2006 | Realyvasquez | A61B 17/072 606/142 |
| 2007/0142906 A1* | 6/2007 | Figulla | A61F 2/2418 623/2.11 |
| 2007/0142907 A1* | 6/2007 | Moaddeb | A61F 2/2445 623/2.11 |
| 2007/0213813 A1 | 9/2007 | Von Segesser et al. | |
| 2008/0071361 A1 | 3/2008 | Tuval et al. | |
| 2008/0208329 A1* | 8/2008 | Bishop | A61B 17/10 623/2.11 |
| 2009/0319037 A1 | 12/2009 | Rowe et al. | |
| 2010/0145438 A1* | 6/2010 | Barone | A61F 2/2418 623/2.1 |
| 2010/0249917 A1 | 9/2010 | Zhang | |
| 2010/0249918 A1 | 9/2010 | Zhang | |
| 2010/0256751 A1 | 10/2010 | Rowe et al. | |
| 2010/0298931 A1 | 11/2010 | Quadri et al. | |
| 2010/0312333 A1 | 12/2010 | Navia et al. | |
| 2011/0029072 A1 | 2/2011 | Gabbay | |
| 2011/0137397 A1 | 6/2011 | Chau et al. | |
| 2011/0178597 A9 | 7/2011 | Navia et al. | |
| 2011/0224785 A1 | 9/2011 | Hacohen | |
| 2011/0264196 A1 | 10/2011 | Savage et al. | |
| 2012/0016464 A1* | 1/2012 | Seguin | A61F 2/2418 623/1.26 |
| 2012/0022640 A1 | 1/2012 | Gross et al. | |
| 2012/0078353 A1* | 3/2012 | Quadri | A61F 2/2418 623/2.11 |
| 2012/0078359 A1* | 3/2012 | Li | A61F 2/0095 623/2.37 |
| 2012/0323316 A1 | 12/2012 | Chau et al. | |
| 2012/0323317 A1* | 12/2012 | Karapetian | A61F 2/2409 623/2.37 |
| 2013/0090726 A1 | 4/2013 | Rowe et al. | |
| 2013/0116779 A1 | 5/2013 | Weber | |
| 2013/0190861 A1 | 7/2013 | Chau et al. | |
| 2013/0211508 A1 | 8/2013 | Lane et al. | |
| 2013/0226289 A1 | 8/2013 | Shaolian et al. | |
| 2013/0274873 A1 | 10/2013 | Delaloye et al. | |
| 2014/0277390 A1* | 9/2014 | Ratz | A61F 2/2418 623/1.26 |
| 2014/0277411 A1 | 9/2014 | Bortlein et al. | |
| 2014/0277412 A1 | 9/2014 | Bortlein et al. | |
| 2015/0257882 A1* | 9/2015 | Bortlein | A61F 2/2418 623/2.11 |
| 2016/0030165 A1* | 2/2016 | Mitra | A61F 2/2409 623/2.42 |
| 2016/0120642 A1 | 5/2016 | Shaolian et al. | |
| 2016/0184095 A1* | 6/2016 | Spence | A61F 2/2418 623/2.11 |

FOREIGN PATENT DOCUMENTS

| | | |
|---|---|---|
| WO | WO 2006/113906 A1 | 10/2006 |
| WO | WO 2008/089365 A2 | 7/2008 |
| WO | WO 2009/026563 A2 | 2/2009 |
| WO | WO 2009/155561 A2 | 12/2009 |
| WO | 2010/008548 A2 | 1/2010 |
| WO | WO 2010/117680 A1 | 10/2010 |
| WO | WO 2010/121076 A2 | 10/2010 |
| WO | WO 2010/127041 A1 | 11/2010 |
| WO | WO 2011/111047 A2 | 9/2011 |
| WO | WO 2011/137531 A1 | 11/2011 |
| WO | WO 2012/063228 A1 | 5/2012 |
| WO | 2013/037519 A1 | 3/2013 |
| WO | WO 2013/120181 A1 | 8/2013 |

OTHER PUBLICATIONS

Oct. 23, 2015 Office Action issued in U.S. Appl. No. 14/204,171.
Jan. 15, 2016 Office Action issued in U.S. Appl. No. 14/204,662.
Jan. 20, 2016 Office Action issued in U.S. Appl. No. 14/204,629.
Feb. 3, 2016 Office Action issued in U.S. Appl. No. 14/204,394.
Nov. 30, 2015 Office Action issued in U.S. Appl. No. 14/204,517.
Boudjemline Younes et al., *Steps Toward Percutaneous Aortic Valve Replacement*, Circulation: Journal of the American Heart Association, 2002, pp. 775-778.
Sep. 13, 2016 Office Action issued in U.S Appl. No. 14/204,327.
Jul. 13, 2016 Office Action issued in U.S. Appl. No. 14/204,394.
Jul. 13, 2016 Office Action issued in U.S. Appl. No. 14/204,629.
Sep. 6, 2016 Office Action issued in U.S. Appl. No. 14/204,662.
Apr. 14, 2016 Office Action issued in U.S. Appl. No. 14/204,662.
Nov. 28, 2016 Office Action issued in U.S. Appl. No. 14/204,394.
Dec. 13, 2016 Office Action issued in U.S. Appl. No. 14/204,629.
Mar. 9, 2017 Office Action issued in U.S. Appl. No. 14/204,662.

* cited by examiner

A-A

B-B

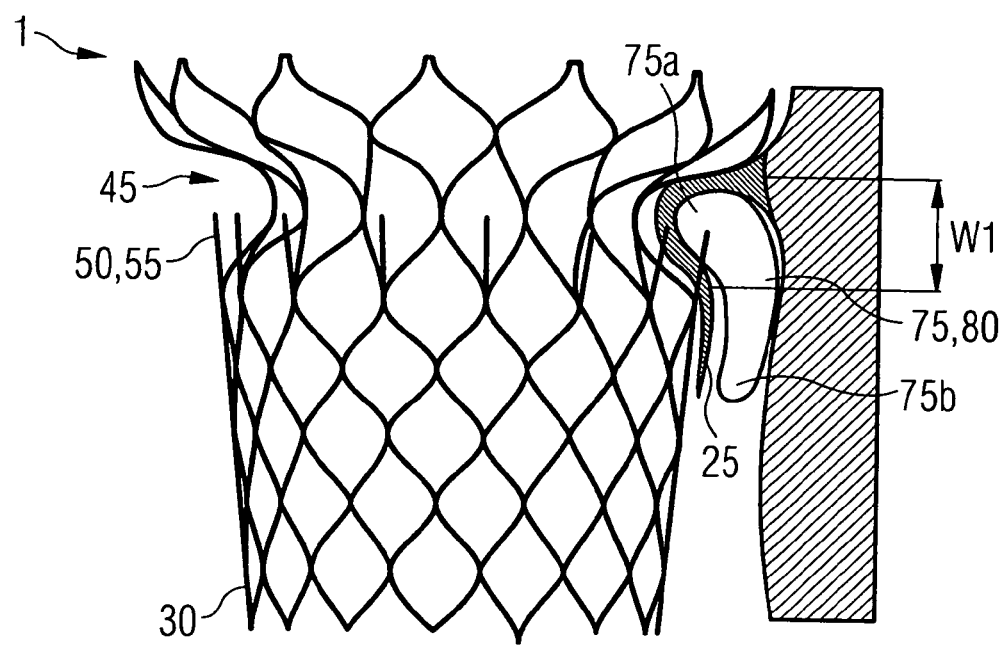

TRANSCATHETER VALVE PROSTHESIS

TECHNICAL FIELD

Embodiments generally relate to a transcatheter valve prosthesis, especially a transcatheter atrio-ventricular valve prosthesis.

BACKGROUND

Heart valve diseases are affecting approximately 300.000 people worldwide each year. Those diseases translate in abnormal leaflet tissue (excess tissue growth, tissue degradation/rupture, tissue hardening/calcifying), or abnormal tissue position through the cardiac cycle (i.e. annular dilation, ventricular reshaping) leading to a degrading valve function like leakage/blood backflow (valve insufficiency) or a resistance to blood forward flow (valve stenosis).

Accordingly, a transcatheter valve prosthesis for functional replacement of a heart valve is desirable.

SUMMARY

Various embodiments of the invention provide a transcatheter atrio-ventricular valve prosthesis for functional replacement of an atrio-ventricular heart valve in a connection channel, having a circumferential connection channel wall structure, between the atrial chamber and the ventricular chamber of a heart, comprising a radially expandable tubular body to be disposed in the interior of the connection channel and extending along an axis, and a valve arranged within and attached to the tubular body, wherein the tubular body is provided with an outer circumferential groove which is open to the radial outside of the tubular body and which defines a groove bottom, whereby the tubular body is separated by the outer circumferential groove into first and second body sections, and wherein the tubular body is provided with a first plurality of projections which extend from the first or second body section in an axial direction of the tubular body and each of which has a free end arranged to overlap the outer circumferential groove, further comprising an elongate outer member to be disposed at the exterior of the connection channel wall structure at a level of the circumferential grove, wherein the outer member can at least partially extend around the tubular body with valve tissue of the connection channel wall structure being correspondingly circumferentially arranged between the tubular body and the outer member and in such a radial distance to the axis of the tubular body that the valve tissue of the connection channel wall structure can be radially forced into the outer circumferential groove so as to be at least partially located radially below the projections.

Various embodiments of the invention further provide a method for implanting a transcatheter atrio-ventricular valve prosthesis comprising a tubular body having a longitudinal axis, a circumferential groove and a plurality of projections each having a free end arranged so as to partially overlap the groove, and an elongate outer member, the method comprising the steps of positioning the tubular body inside a connection channel between an atrial and a ventricular chamber of a heart, positioning the elongate outer member on an outside of the connection channel at an axial level of the circumferential groove, and fixating the prosthesis relative to the heart by reducing a distance between the elongate outer member and the tubular body so that tissue of the connection channel is inserted into the groove so as to at least partially be radially inside the projections with respect to the axis.

BRIEF DESCRIPTION OF THE DRAWINGS

In the drawings, like reference characters generally refer to the same parts throughout the different views. The drawings are not necessarily to scale, emphasis instead generally being placed upon illustrating the principles of the invention. In the following description, various embodiments are described with reference to the following drawings, in which.

DESCRIPTION

Figure 1:
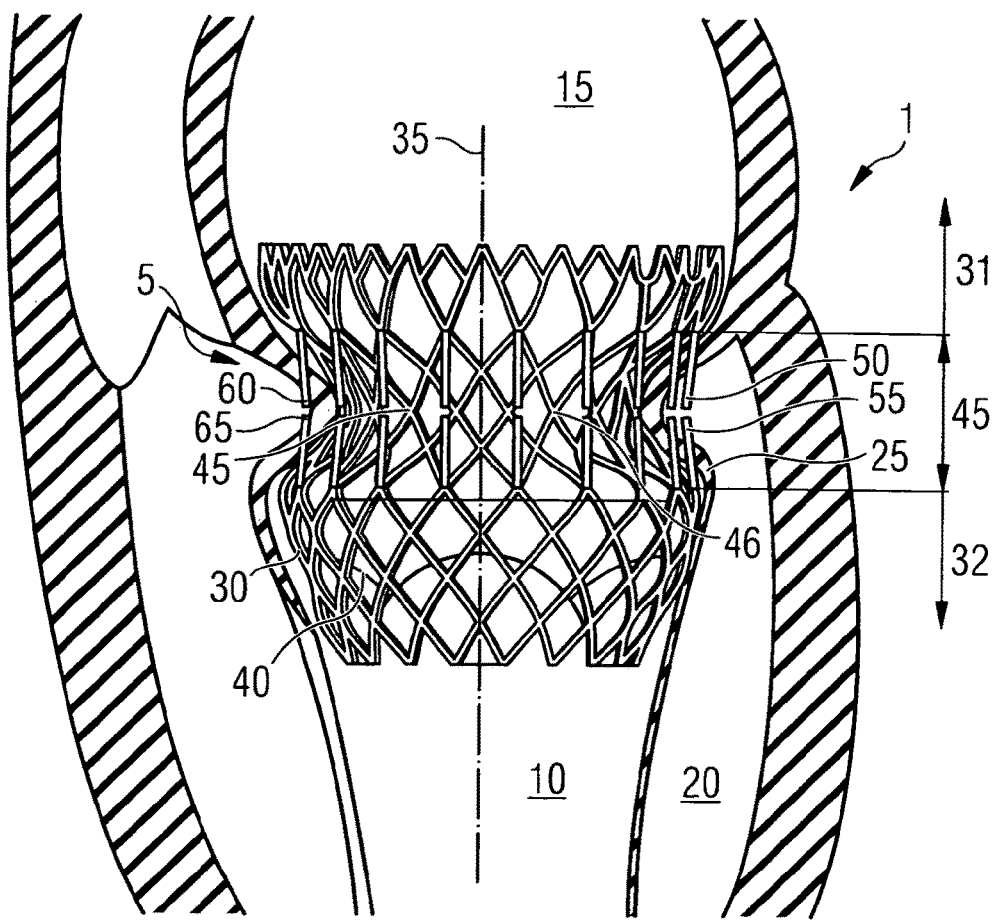
FIG. 1 shows schematically a transcatheter valve prosthesis according to an embodiment located in a connection channel of a human heart.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, logical, and electrical changes may be made without departing from the scope of the invention. The various embodiments are not necessarily mutually exclusive, as some embodiments can be combined with one or ore other embodiments to form new embodiments.

With reference to FIGS. 1, 1a, 1b and 2, a transcatheter atrio-ventricular valve prosthesis 1 for functional replacement of a (native) atrio-ventricular heart valve 5 in a connection channel 10 that connects an atrial heart chamber 15 with a ventricular chamber 20 and comprising a connection channel wall structure 25 may comprise a tubular body 30. The tubular body 30 may be disposed in the interior of the connection channel 10 and extend along an axis 35. The axis 35 may be the longitudinal axis 35 of the tubular body 30 which may be an elongated body. In the implanted condition, the axis 35 of the tubular body 30 may be aligned substantially coaxial to an axis of the connection channel 10. The tubular body 30 may be radially compressible so as to facilitate approach to and insertion into the connection channel 10, e.g. using a catheter or the like, and then be radially expandable so as to closely engage the interior or inner side of the connection channel wall structure 25, and may comprise an artificial heart valve 40 (e.g. schematically shown in FIG. 6a) arranged within the tubular body 30.

The native atrio-ventricular heart valve 5 (e.g. a mitral valve or a triscupid valve) to be replaced has the generally circumferential wall structure 25 forming the connection channel 10 or through opening between the atrial 15 and ventricular 20 chambers of the heart and including a circumferential valve annulus, valve leaflets opening and closing the connection channel/through opening and closing the connection channel 10/through opening at a position close to the valve annulus, a generally circumferential cord structure (chordae tendinae) connected between the valve leaflets and generally circumferential papillary muscle(s), and said circumferential papillary muscle(s).

The artificial heart valve 40 may be attached to the tubular body 30 and may be designed to serve as an artificial replacement valve for an atrio-venticular heart valve (for example a mitral and/or a tricuspid valve). The artificial valve 40 may comprise artificial flaps (e.g. three flaps as schematically shown in e.g. in FIG. 6a) for functional replacement of the native heart valve. The tubular body 30 may be provided with an outer circumferential groove 45. The outer circumferential groove 45 may be open to the radial outside of the tubular body 30. The circumferential groove 45 may define a groove bottom 46. The outer circumferential groove 45 may define a channel 47 which is defined itself by the groove bottom 46 and axially (in axial direction of the tubular body 30) opposite side walls 48, 49. The groove bottom 46 may separate the tubular body 30 in first and second body sections 31, 32. The circumferential groove 45 may extend around a whole circumference of the tubular body 30 or may only extend partially around a circumference of the tubular body 30. The outer circumferential groove 45 may be a continuous that is non-interrupted groove, but may also be an interrupted groove 45 having, for example, two or more circumferential groove portions 45 provided, for example, on the same axial level of the tubular body 30 that are interrupted by areas in which no recessed portion, which may provide groove portion, is formed. The circumferential groove 45 may have an axial distance (along axis 35) from the axial ends of the tubular body 30, i.e. the circumferential groove 45 may be formed spaced apart in an axial direction from end portions of the tubular body 30.

As shown in FIG. 1, the first body section 31 may be the part of the tubular body 30 that is located above (e.g. proximal from) the circumferential groove 45, and the second body section 32 may be the part of the tubular body 30 that is located beneath (e.g. distal from) the circumferential groove 45. Both of the first and second body sections 31, 32 may have a generally cylindrical shape. According to a variation, the first body section 31 may have a conical shape along the axis of the tubular body, with its cross-section diameter increasing from the groove 45, and the second body section 32 may be generally cylindrical. According to a variation, both of the first and second body sections 31, 32 may have a conical shape along the axis of the tubular body, with their respective cross-sectional diameter increasing from the groove 45. According to variations, the cross sections (along axis 35) of sections 31 and/or 32 may be or contain non circular shapes but elliptical shapes or D-shaped cross sections. In addition, the direction of curvature in the axial profile (seen in a axial section along the tubular body 30) between the groove 45 and the first body section 31 and/or between the groove 45 and the second body section 32 may change (from concave curvature of the groove 45 to a convex curvature at the transition between groove 45 and first and/or second body section 31, 32). The axially opposite side walls 48, 49 of the groove 45 may be part of the first and second, respectively, body sections 31, 32 and may axially delimit the first and second, respectively, sections 31, 32 towards the channel 47 of the groove 45, as it is shown e.g. in FIG. 8. A radial diameter of the first body section 31 (e.g. at an end portion that is opposite to the second body section 32) of the tubular body 30 may be larger than any diameter of the second body section 32. This may allow to more efficiently fixate the prosthesis 1 in the connection channel 10 as the first body section 31 having a larger diameter may provide a better hold of the prosthesis 1 in the connection channel 10 by providing a friction and/or (mere) form fit (e.g. caused by the first body section 31 being located in the atrial chamber 15 and having a diameter larger than a diameter of the connection channel 10).

Further, the valve prosthesis 1 may comprise a first plurality of projections 50 and a second plurality of projections 55. The projections 50, 55 may extend from the first and second sections 31, 32, respectively, in opposite axial directions, that is they extend, at least with an extension component or an extension vector, in a direction along the axis 35 (e.g. the longitudinal axis 35) of the tubular body 30. Accordingly, the first projections 50 and the second projections 55 extend generally towards each other, whereby they may not extend exactly or in line towards each other, but with an extension vector. The projections 50, 55 may extend substantially parallel to the axis 35 of the tubular body 30 or may also extend in a (lateral) angle γ to the axis 35 of the tubular body 30, wherein the (lateral) angle γ extends tangential to the circumference of the tubular body 30, as it is shown e.g. in FIG. 2a.

Figure 11A:
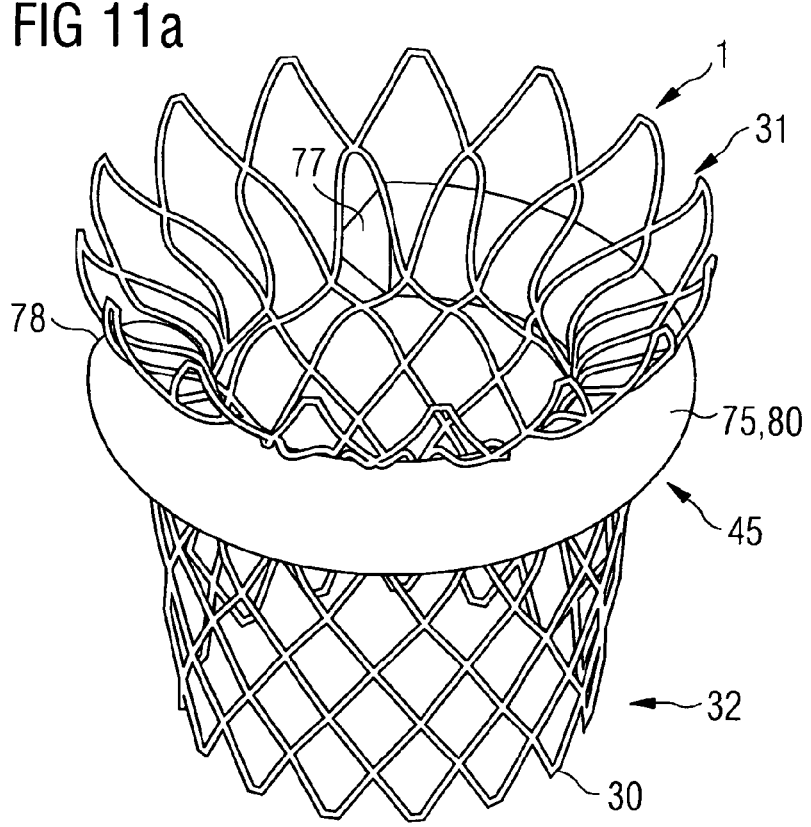
Figure 11B:
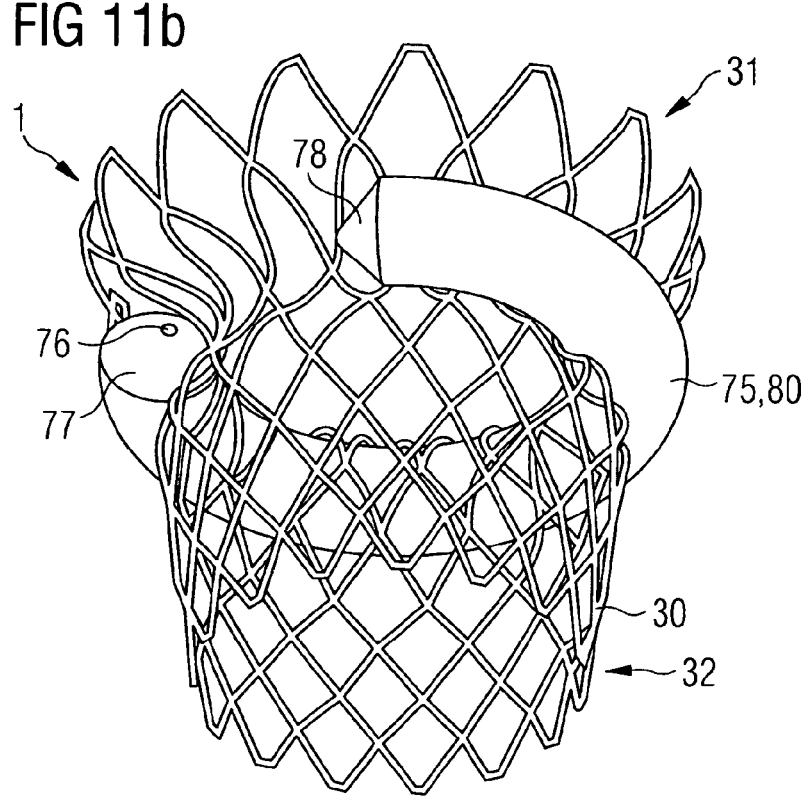
Figure 11C:
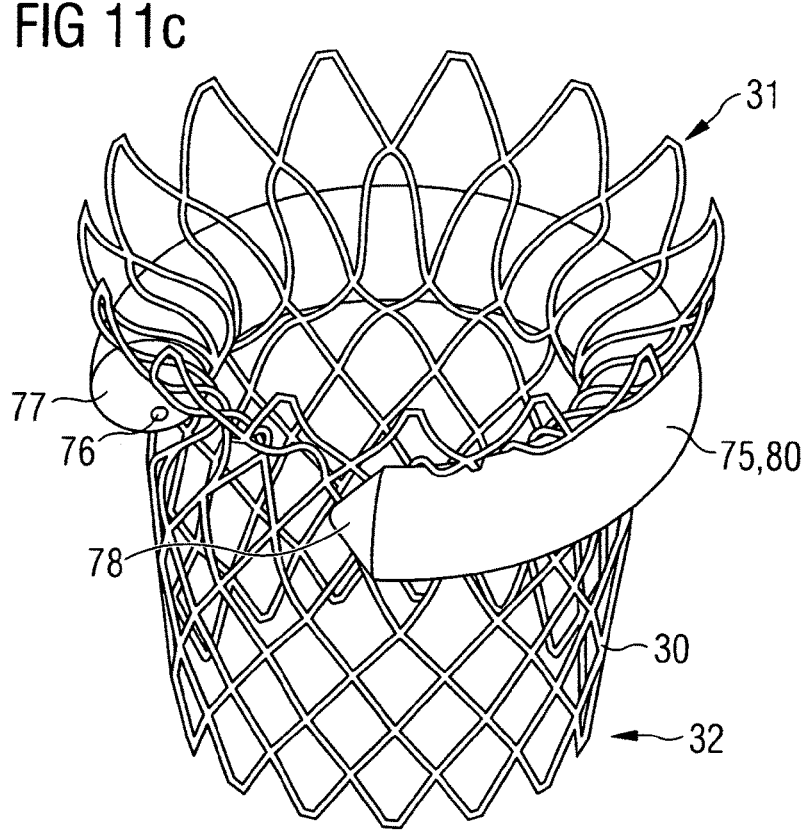
Figure 11D:
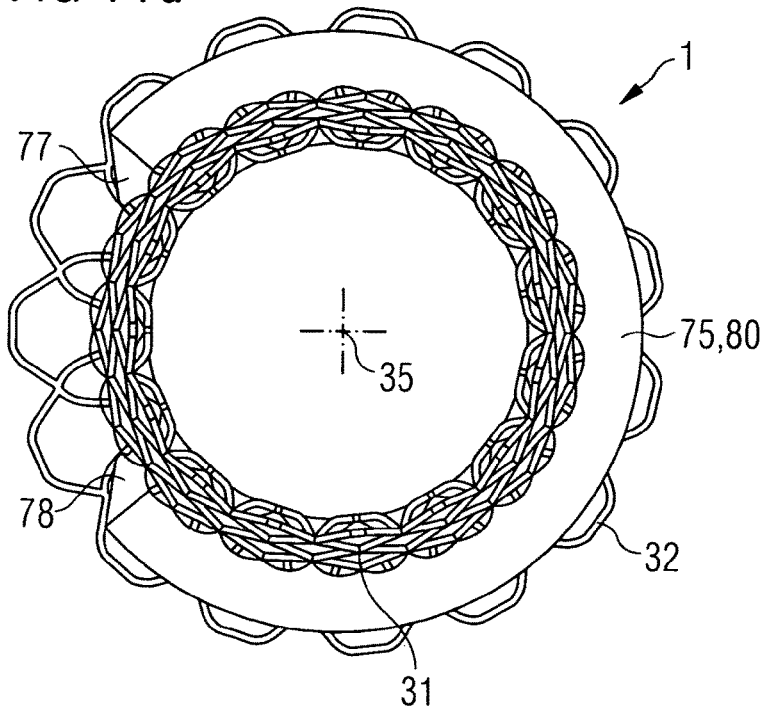

The valve prosthesis 1 may comprise one plurality of projections 50, 55 only that may extend from the first or second sections 31, 32 in an axial direction of the tubular body 30 and may overlap the circumferential groove 45. With reference to e.g. FIGS. 11a-c, the valve prosthesis 1 may not comprise any projections 50, 55 and the circumferential groove 45 may be provided with (e.g. integrally formed on) the tubular body 30.

The projections of the first plurality of projections 50 each may have free ends 60, and the projections of the second plurality of projections 55 each may have free ends 65. The free ends 60, 65 of the first and the second plurality of projections 50, 55 may be arranged so as to overlap the outer circumferential groove 45. That is, the free ends of the first and second plurality of projections 50, 55 are arranged at an axial level of the groove 45 so as to overlap the groove 45.

The first and second plurality of projections 50, 55 as such may at least partially or completely overlap the groove 45 along their extension.

The first 50 and second 55 pluralities of projections may extend in a radial distance radially outwards of the bottom 46 of the groove 45 so that a hollow (circumferential) chamber 66 is defined between the groove bottom 46 and the first and second plurality of projections 50, 55 in the channel 47. The opposite side walls 48, 49 may further define the hollow chamber 66 in axial direction of the tubular body 30. Hence, the hollow chamber 66 may be confined radially by the pluralities of projections 50, 55 and the groove bottom 46 and axially by opposite sidewalls 48, 49 (e.g. top- and bottom-walls) of the groove 45.

A method of using a transcatheter valve prosthesis 1 may comprise positioning it in the connection channel wall structure 25 of a heart and then inserting tissue that is adjacent to the circumferential groove 45, of the connection channel wall structure 25 into the circumferential groove 45 to be placed radially below the first and second plurality of projections 50, 55. The tissue can then be held in place in the circumferential groove 45 by the first 50 and/or second plurality of projections 55, which, if, for example, provided with acute or sharpened ends, may penetrate into the tissue which from its position below may be biased back to its initial radial position. The prosthesis 1 may be positioned such that its outer circumferential groove 45 is at the level of the annulus of the circumferential wall structure 25 or adjacent thereto towards the side of the ventricular chamber 20. By the first and second plurality of projections 50, 55 keeping the tissue within the groove 45, the transcatheter valve prosthesis 1 can be positioned and fixated relative to the heart. Further, since the first and second plurality of projections 50, 55 axially extend towards each other, the prosthesis is further safely and reliably prevented from being axially pushed out of the connection channel 10 by the pumping activity of the heart. The first 50 and/or the second 55 plurality of projections may keep the tissue of the connection channel wall structure 25 in the circumferential groove 45 by perforating it (e.g. transfixing it, e.g. skewering it) and/or by an interference fit. The tissue that is held in the circumferential groove 45 may also (partially or fully) seal the transcatheter valve prosthesis 1 against the interior of the connection channel 10 so that blood, e.g. pressurized blood, can only flow through the tubular body 30 (and the artificial heart valve 40 therein) but can not bypass the tubular body 30 on its exterior side (i.e. between the exterior of the tubular body 30 and the interior of the connection channel wall structure 25). In this respect, the inner and/or outer circumferential surface of the tubular body 30 may additionally be provided with an impermeable layer, for example in form of a liner 33b.

The prosthesis 1 may be located in the connection channel 10 so that the circumferential groove 45 is located on the ventricular side of the annulus of a natural valve, e.g. having a distance from the natural valve annulus, i.e. the circumferential groove 45 may be a sub-annular circumferential groove and/or the prosthesis 1 may be a sub-annular-prosthesis 1. The prosthesis 1 may be adapted to be a sub-annular prosthesis. That is, the tubular body 30 may have a transverse dimension (also referred to as diameter herein) at an axial level (with respect to axis 35) that is smaller than a transverse dimension of a natural valve annulus and/or transverse dimension and/or axial lengths of the tubular body may be suitable so that the first body section 31 may be located in an atrial chamber 15 and that the second body section 32 may be located in the connection channel 10 with the groove 45 being located on a ventricular side of the natural valve annulus having a distance to said annulus.

Only one circumferential groove 45 as described above may be provided on the tubular body 30. However, an elongated prosthesis 1 having two or more circumferential grooves 45 may be provided, wherein a respective set of first and a second plurality of projections 50, 55 as described above may be arranged and assigned to the respective one of the two or more grooves 45. The groove 45 or the respective groove may be formed by the first and second body sections 31, 32 of the tubular body 30 as such, wherein the projections 50 and/or 55 may not be involved in forming the (respective) groove 45 as such. There may also be embodiments (see further below), in which the projections 50 and/or 55 are at least partially in forming the groove 45, for example on the side of the tubular body 30 that is proximal to the ventricular chamber 20.

Figure 6A:
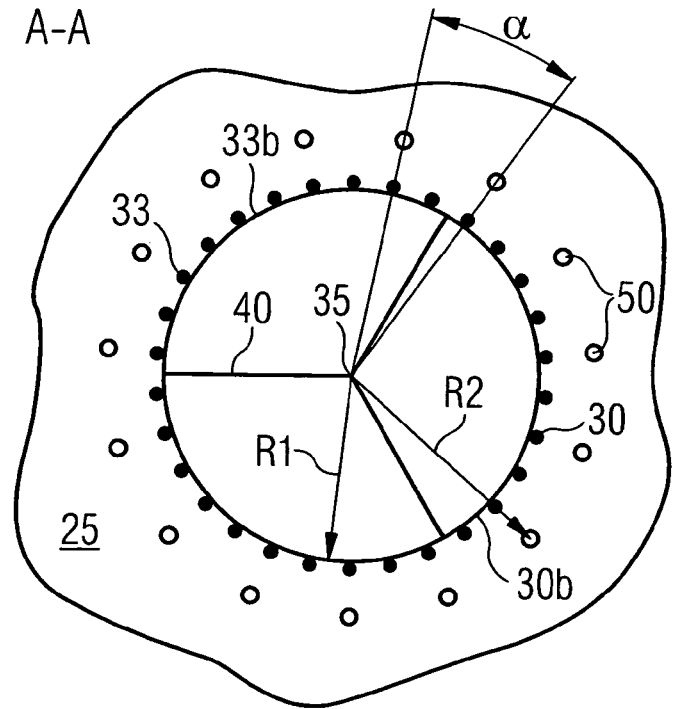
FIG. 6a shows a schematic cross section of a transcatheter valve prosthesis along A-A in FIG. 3.

The tubular body 30 may comprise or may be a mesh-type body having elongate mesh or grid elements 33 crossing each other at crossings 34. The mesh elements 33 may be formed from wires comprising steel and/or a superalloy and/or a shape memory alloy (e.g. nitinol) and/or nickel and/or titanium and/or precious metals (e.g. gold) and/or alloys comprising the aforementioned. The mesh elements 33 may also comprise other alloys or may be made from organic material, e.g. polymers. The mesh elements 33 may e.g. be made from polyvinyl-chloride and/or polystyrene and/or polypropylene or another polymer. The tubular body 30 may be from a shape-memory material which expands when experiencing usual body temperature. The tubular body 30 may be self-expandable. The tubular body 30 may also be not self-expandable, but expandable by a balloon or another expansion mechanism. Correspondingly, the tubular body 30 may be compressible to be insertable via the catheter and may then be expandable when appropriately positioned with the connection channel wall structure 25. The tubular body 30 may comprise the above-mentioned liner 33b (c.f. FIG. 6a) attached to the mesh elements 33 made from the same or made from different materials. The liner 33b may be disposed on an interior side or art exterior side of the mesh elements 33 and/or tubular body 30 and may cover the circumference of the tubular body 30 fully or only partially in axial direction 35 and/or in circumferential direction.

The circumferential groove 45 of the tubular body 30 and/or the projections of the first and/or the second plurality of projections 50, 55 may interact with the connection channel wall structure 25 so as to fixate the valve prosthesis 1 with respect to the channel wall structure 25 and the connection channel 10. Tissue of the channel wall structure 25 may be "caught" in the circumferential groove 45 and be held in place by the free ends 60, 65 of the first and/or the second plurality of projections 50, 55 which may serve as hook elements. The tissue of the channel wall structure 25 may be perforated by the free ends 60, 65 and thereby held more firmly in the circumferential groove 45 of the tubular body 30, wherein the tissue may also be held in the groove 45 by means of an interference and/or clamping fit between the projections 50 and/or 55 (or part thereof) and the tissue of the connection channel wall structure 25. In order to allow the first and/or second plurality of projections 50, 55 to penetrate the tissue of the circumferential connection channel wall structure 25, which has been forced into the groove, the free ends of a plurality or of each of the first 50 and/or second 55 pluralities of projections may be an acute or sharpened end. The projections of the first and/or second plurality of projections 50, 55 each or some thereof may be pins.

Figure 1A:
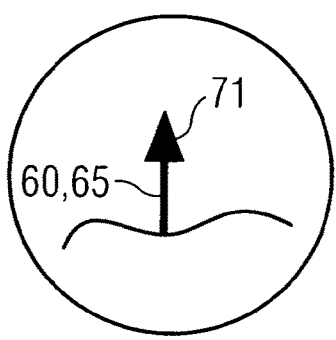
FIG. 1a shows a detail of a free end of a projection of the valve prosthesis according to a variation.
Figure 1B:
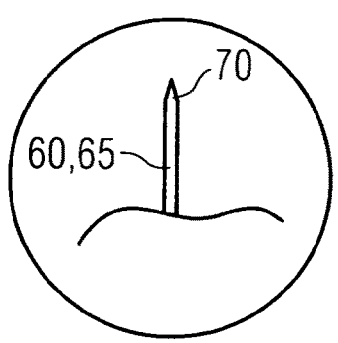
FIG. 1b shows a detail of a free end of a projection of the valve prosthesis according to a variation.

With further reference to FIG. 1b, the free ends 60, 65 of the first and/or the second plurality of projections 50, 55 may be conical ends 70 so as to be able to perforate tissue of the connection channel wall structure 25. According to a variation, the free ends 60, 65 of the first and/or the second plurality of projections 50, 55 may also be blunt. The free ends 60, 65 and/or the first and/or second plurality of projections 50, 55 may be pin-shaped.

Some or all of the free ends 60, 65 of the projections 55, 60 may comprise barbs or hooks 71 as shown in FIG. 1a. The hooks 71 may serve to perforate tissue of the connection channel wall structure 25 and prevent the tissue from slipping off the free end 60, 65. Thereby tissue that is perforated by barbs or hooks 71 disposed on a free end 60, 65 is unable to slip from the free end 55, 65 resulting in tissue from the heart valve connection channel wall structure 25 being caught even more reliably in the circumferential groove 45. Some or all of the free ends 60, 65 may be blunt or may have conical ends 70 or comprise barbs or hooks 71. The first 50 or second 55 plurality of projections may comprise different types of free ends 60, 65 according to the anatomical conditions, but may also comprise the same type of free ends 60, 65.

The free ends 60, 65 and/or the first 50 and second pluralities 55 of projections may be arranged in different axial and/or radial positions and orientations with respect to each other. With reference to FIGS. 1 and 6a, each projection of the first plurality of projections 50 may have the same circumferential angular distance a (that is an angular distance between two radial directions extending from longitudinal axis 35 of the tubular body 30) from each other, i.e. the projections 50 may be equally circumferentially spaced. However, the projections of the first plurality of projections 50 may also have different angular distances a from each other, i.e. be not spaced evenly around a circumference of the tubular body. Although not shown in FIGS. 6a-c, similarly, each projection of the second plurality of projections 55 may have the same angular distance from each other, i.e. be spaced equally around a circumference of the tubular body 30. However, the projections of the second plurality of projections 55 may also have different circumferential angular distances a from each other, i.e. be not spaced evenly around a circumference of the tubular body.

Figure 3:
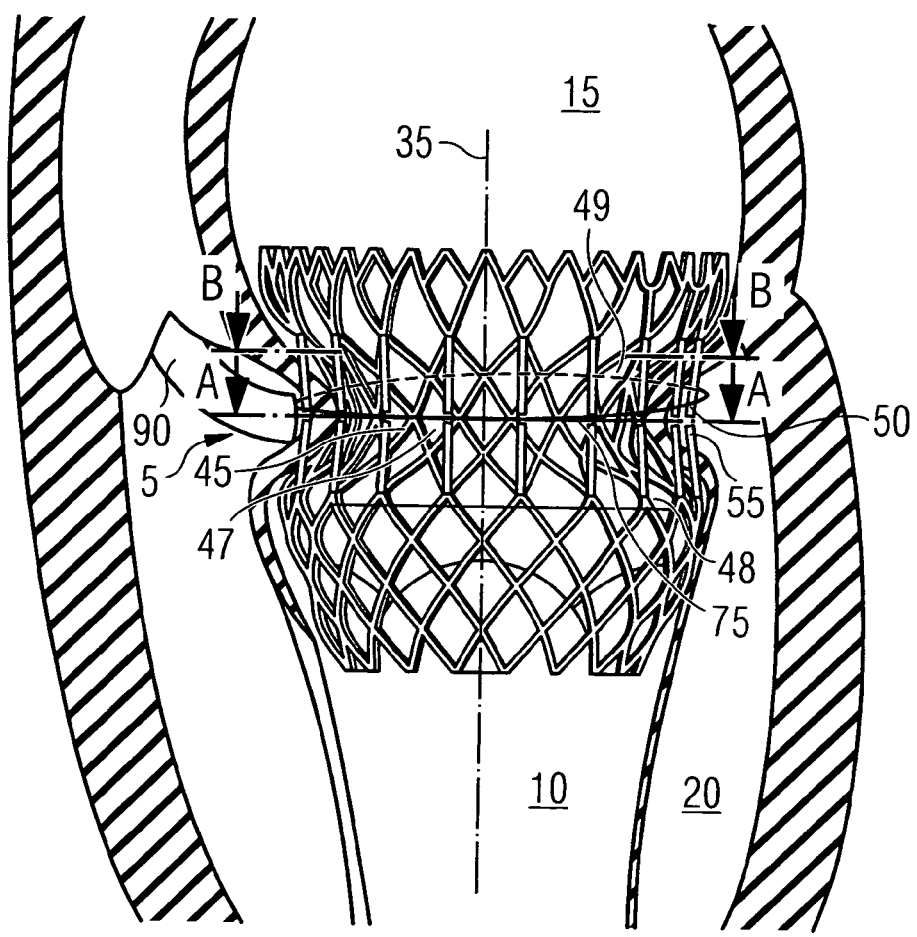
FIG. 3 shows schematically a transcatheter valve prosthesis comprising an elongate outer member according to an embodiment located in a connection channel of a human heart.

The first plurality of projections 50 may be arranged with respect to the second plurality of projections 55 on the tubular body 30 in a way that each projection of the first plurality of projections 50 is substantially on the same radial level (that is the same radius, e.g. R2) as a projection of the second plurality of projections 55 (as it is shown e.g. in FIGS. 1 and 3). On the other hand, each projection of the first plurality of projections 50 may be arranged on a different radius than a projection of the second plurality of projections 55, wherein the first plurality of projections 50 may each be on a same radius, and wherein the second plurality of projections 55 may each be on a same radius.

With, for example, reference to FIGS. 1 and 3, the first plurality of projections 50 and the second plurality of projections 55 may extend so as to be aligned or coaxial to each other. The first plurality of projections 50 may also not be aligned with the second plurality of projections 55, wherein the first plurality of projections 50 may themselves extend substantially parallel to each other or may not, and wherein the second plurality of projections 55 may themselves extend substantially parallel to each other or may not.

Figure 2:
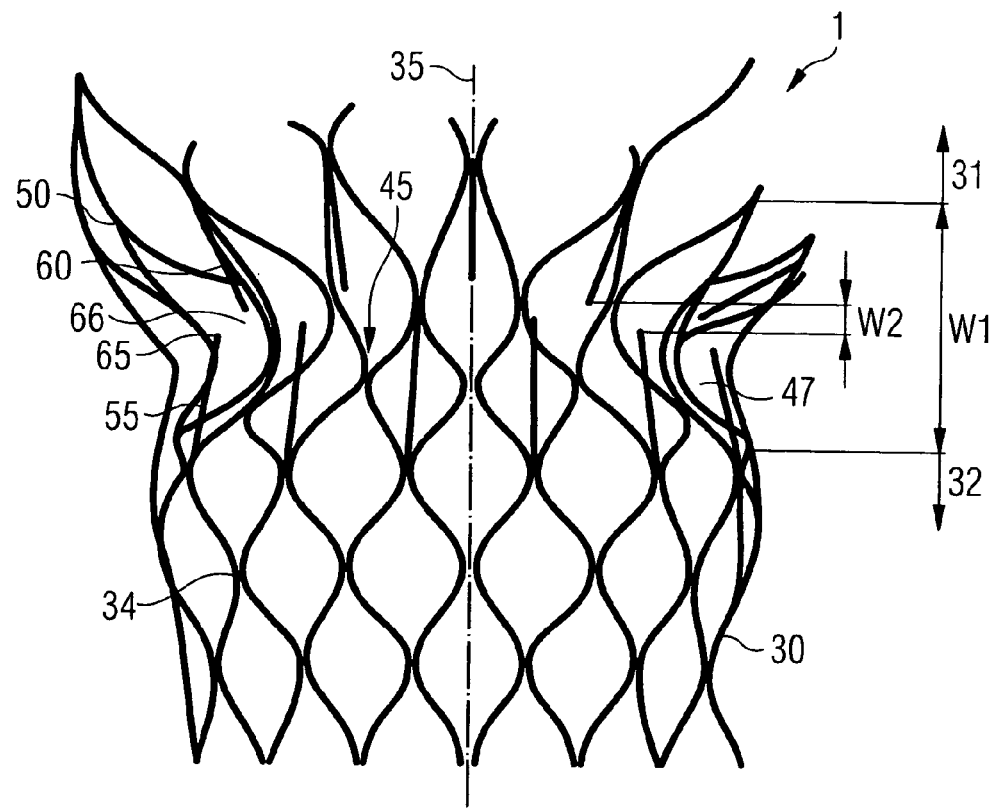
FIG. 2 shows a transcatheter valve prosthesis according to an embodiment, FIG. 2a schematically shows extension angles of projections according to an embodiment.
Figure 4:
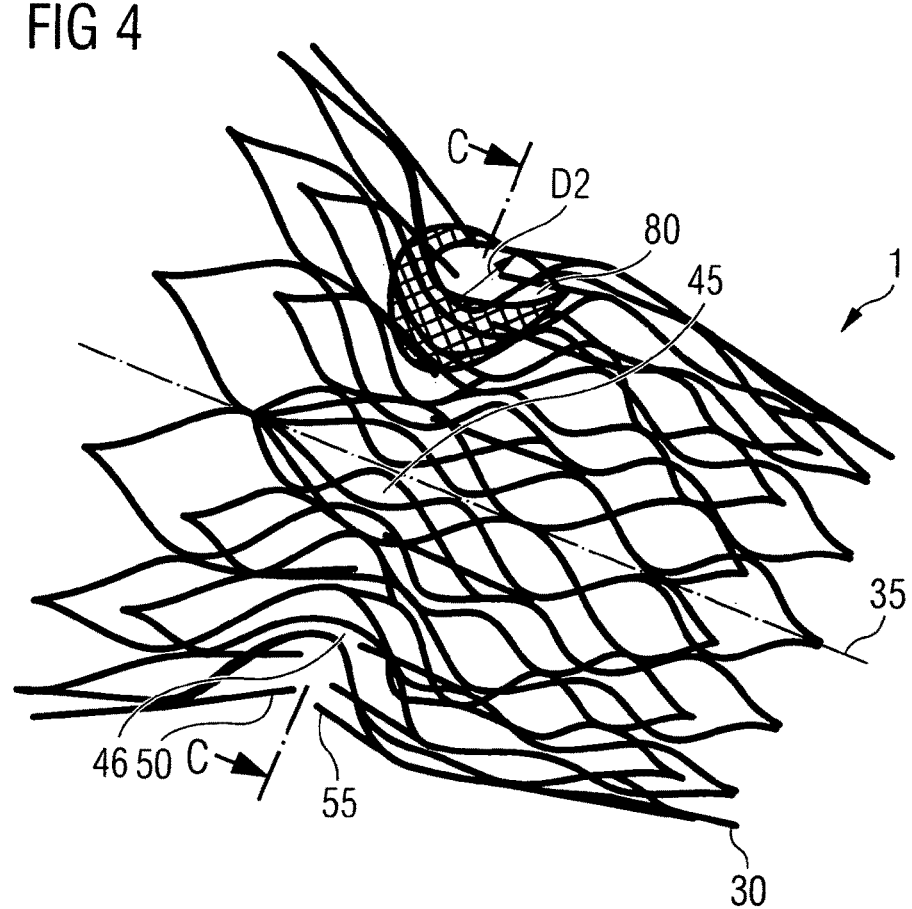
FIG. 4 shows a transcatheter valve prosthesis including a clamping member according to an embodiment.

With, for example, reference to FIGS. 2 and 4, the first and second plurality of projections 50, 55 may be arranged in circumferential direction in an alternating manner, wherein for example each first projection 50 is circumferentially between two second projections 55 (and the other way round). There may also be other appropriate circumferential arrangement patterns for the first and second plurality of projections 50, 55, wherein, for example, sets of first projections 50, of for example one, two, three, four, or more first projections 50, are arranged between sets of second projections 55, of for example one, two, three, four or more second projections 50.

The number of the projections of the first plurality of projections 50 and the number of projections of the second plurality of projections 55 may be, for example, in a range of three to five, or eight to ten, fifteen to twenty, thirty to hundred or more or may be any other number. The first plurality of projections 50 may comprise the same number of projections or another number of projections as the second plurality of projections 55 or vice versa.

Figure 9A:
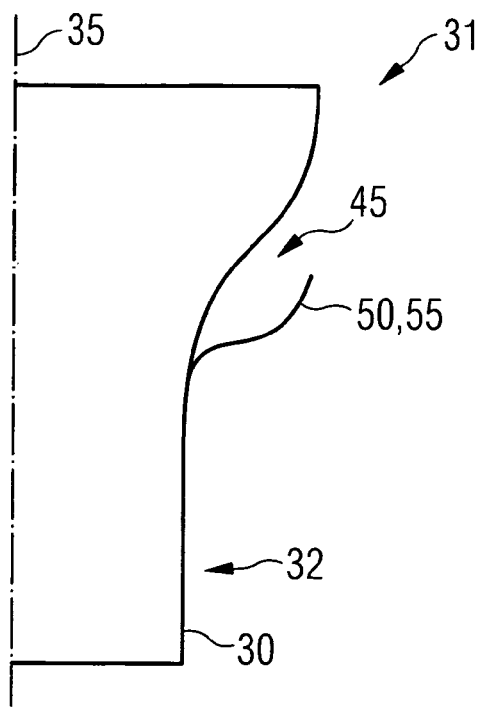
FIG. 9 shows a tubular body of a transcatheter valve prosthesis, FIG. 10 schematically shows the transcatheter valve prosthesis including an outer member, and FIG. 11 schematically shows the transcatheter valve prosthesis including an elongate outer member according to a variation.
Figure 9B:
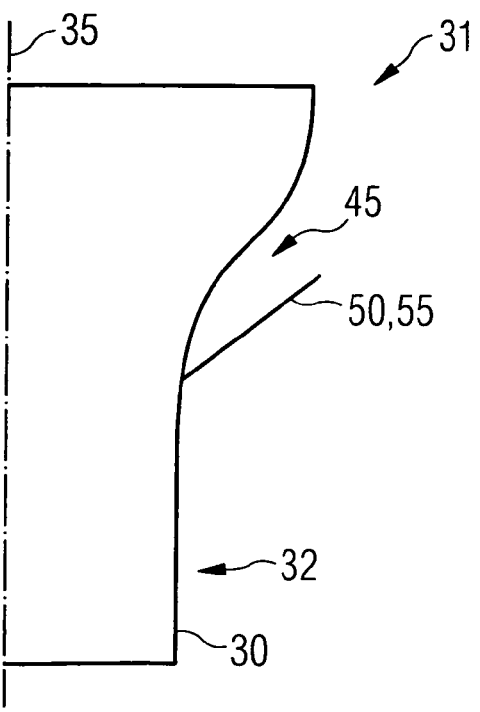

The projections of the first plurality of projections 50 and/or the projections of the second plurality of projections 55 may extend from the tubular body 30 from positions, where mesh elements 33 of the tubular body 30 are crossing with each other at the crossings 34. This may improve the mechanical stability of the interconnection of the tubular body 30 with the projections 50, 55. The projections 50, 55 may e.g. be welded, soldered and/or braided to the tubular body 35. They may also be sutured, bonded or glued to the tubular body 35. As an alternative or additionally, the projections 50, 55 may also be monolithically integrally formed with the tubular body 30. That is, with reference to e.g. FIGS. 9a and 9b, the projections 50,55 (or any one or bath of the pluralities of projections) may be formed by mesh elements 33 that are not connected to another mesh element 33 at a crossing 34 but are projecting from the tubular body 30 (e.g. caused by bending the mesh element 33) in a radial and/or axial direction with respect to longitudinal axis 35 so as to form a projection 50, 55. Further, projections 50, 55 (e.g. monolithically integrally formed by mesh elements 33 or provided separately and connected with the tubular body 30) may form the circumferential groove 45 by projecting radially and axially from the tubular body 30 with respect to its longitudinal axis 35. Accordingly, by facing away from the tubular body 30, the projections may define a circumferential groove 45 on the tubular body 30. The circumferential groove 45 may also be further defined by a generally conical or similar shape of a body section (e.g. first body section 31 and/or second body section 32) of the tubular body 30 that has a cross-sectional diameter that is increasing from the groove 45 in a direction of longitudinal axis 35. As seen e.g. in FIGS. 9a and 9b, the generally conical shape of a body section 31, 32 may accordingly interact with the projections 50, 55 which are projecting from the tubular body 30 so as to further define the circumferential groove 45. FIG. 9a shows projections 50, 55 that define a circumferential groove 45 by projecting first in a substantially radial direction relative to the longitudinal axis 35 and then in a substantially parallel direction to the longitudinal axis 35 when seen from the point from which the projections extend from tubular body 30. FIG. 9b shows projections 50, 55 that extend generally rectilinearly to define the circumferential groove 45. The projections 50, 55 may be made from the same materials that were described above with reference to the tubular body 30, e.g. super alloys, e.g. shape memory alloys (like nitinol) or steel or titanium (or alloys comprising titanium) or organic material like polymers, or the projections may be made from different material or materials.

Figure 8:
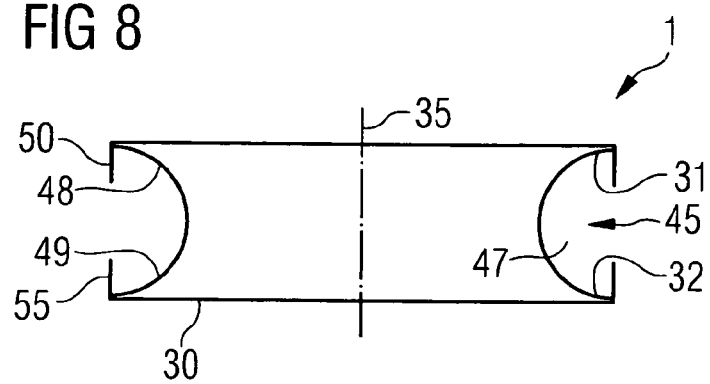
FIG. 8 shows a transcatheter valve prosthesis according to an embodiment.

As can be seen e.g. from FIG. 8, all or some projections of the first plurality of projections 50 and/or all or some projections of the second plurality of projections 55 may be extending in (e.g. along) a substantially straight line or in a straight line, i.e. they may not comprise any longitudinal curvature from the point from which they extend from the tubular body 30 to their respective free end 60, 65, i.e. they may extend rectilinearly. They may, however, nevertheless comprise barbs or hooks 71 and/or may be pin-shaped. The first plurality of projections 50 may extend from substantially the same axial level (relating to the axial direction of the tubular body 30) from the tubular body 30 (e.g. shown in FIGS. 1 to 3) or may extend from different axial levels from the tubular body 30. Correspondingly, the second plurality of projections 55 may extend from substantially the same axial level (relating to the axial direction of the tubular body 30) from the tubular body 30 (e.g. shown in FIGS. 1 to 3) or may extend from different axial levels from the tubular body 30. The axial extension of the first plurality of projections 50 (axial distance (along axis 35 of tubular body 30) between base of projection on the tubular body and free end of projection) and/or of the second plurality of projections 55 may be substantially the same or may be different, and the extension or length of the first plurality of projections 50 and/or of the second plurality of projections 55 (distance between basis of the projection 50, 55 on the tubular body 30 and the free end 60, 65 of the projection 50, 55) may be the same or may be different.

In addition to the first and second plurality of projections 50, 55 the tubular body 30 may be provided with any other type of projection and/or collar.

The first 50 and the second plurality 55 of projections may extend from the first 31 and the second 32 body sections, respectively, from areas that are adjacent to or are bordering the radial outer circumference of the circumferential groove 45. The first 50 and the second plurality 55 of projections may extend from the opposite side walls 48, 49 laterally defining the groove 45.

Referring to FIG. 2, the free ends 60 of the first 50 plurality of projections may be axially spaced from the free ends 65 of the second 55 plurality of projections by an axial distance W2 in a direction of the axis 35 of the tubular body 30. The free ends 60 of first plurality of projections 50 may be arranged on a same axial level or on different axial levels, and the free ends 65 of the second plurality of projections 55 may be arranged on a same axial level or on different axial levels.

In case a transcatheter valve prosthesis 1 comprises one plurality of projections 50, 55, the axial distance W2 may define a distance of one or more or all of the free ends 60, 65 of the (one) plurality of projections 50, 55 to a side all 48, 49, that is opposite to the respective body section 31, 32 the plurality of projections extending from, of the circumferential groove 45.

The projections of the first plurality of projections 50 may axially overlap with the projections of the second plurality 55 of projections with each other (not shown), wherein there may be defined an axial overlapping-distance between the free ends 60 of the first plurality of projections 50 and the free ends 65 of the second plurality of projections 55. Some free ends 60 of the first plurality of projections 50 may be axially spaced from corresponding free ends 65 of the second plurality of projections 55, while other free ends 60 and 65 may be arranged so as to axially overlap each other.

Figure 2A:
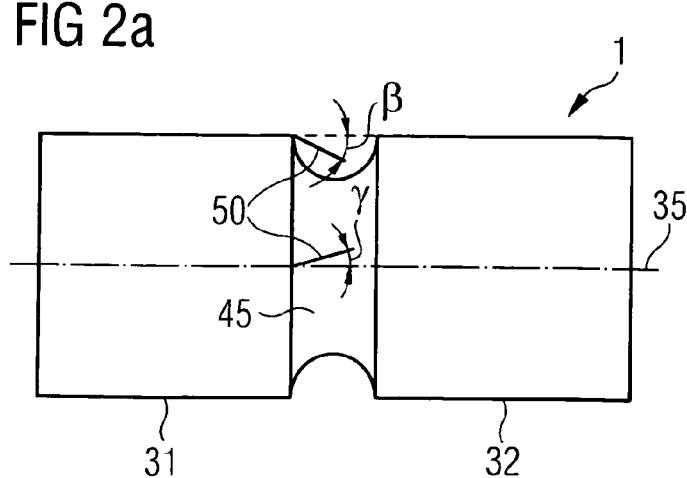

With reference, for example, to FIG. 2a, the projections 50, 55 (each) may extend in a manner so as to be radially and inwardly inclined by an angle β, thereby obliquely extending into the outer circumferential groove 45. The angle β defining the radial and inward inclination of the projections 50, 55 with respect to the axis 35 of the tubular body 30 may be an acute angle, for example in a range of equal or smaller than 45° or equal or smaller than 30°, or equal or smaller than 15°. Only a part or number of the first projections 50 and/or only a part or number of the second projections 55 may radially and inwardly inclined as above described.

FIG. 6a, which corresponds to the cross section along A-A shown in FIG. 3, illustrates the interaction of heart valve tissue of the connection channel wall structure 25 and the first plurality of projections 50 (a cross-section transverse the axis 35 and through the second plurality of projections 55 would result in a similar depiction as shown in FIG. 6a). The first plurality of projections 50 can be seen perforating tissue of the connection channel wall structure 25 to thereby more reliably prevent it from retracting from the tubular body 30 of the prosthesis 1, which results in the prosthesis 1 being held more firmly in its intended place.

Figure 6B:
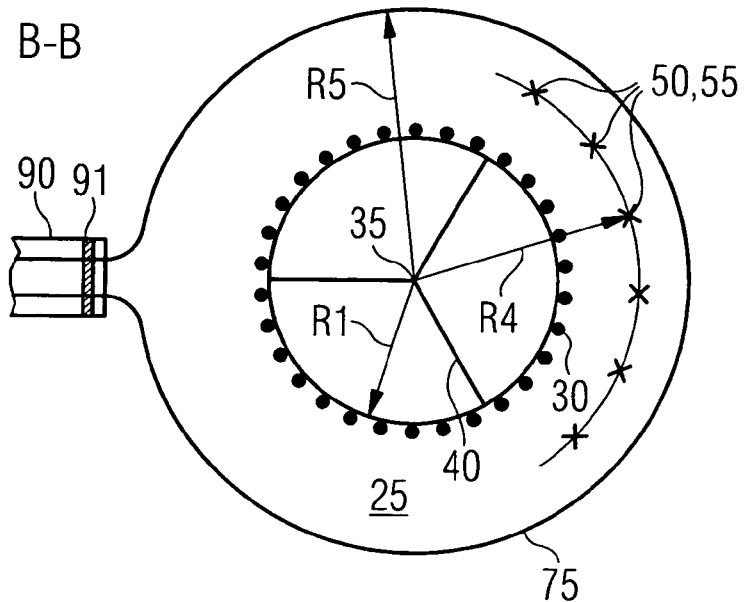
FIG. 6b shows a schematic cross section of a transcatheter valve prosthesis along BB in FIG. 3.

With further reference to FIG. 3 and FIG. 6b, the transcatheter atrio-ventricular valve prosthesis 1 may further comprise an elongate outer member 75. The elongate outer member 75 may be disposed at the exterior of the connection channel wall structure 25 (i.e. e.g. in the ventricular chamber 20) at an axial level (e.g. with respect to axis 35) of the circumferential groove 45 of the tubular body 30. The elongate outer member 75 may extend at least partially around, for example completely and continuously circumferentially around, the tubular body 30 and may be handled e.g. using a catheter member 90 that is shown schematically in FIG. 6b. A radial distance R5 between the longitudinal axis 35 and the elongate outer member 75 may be reducible or reduced so that the valve tissue of the connection channel wall structure 25 can be correspondingly at least partially forced into the outer circumferential groove 45 so as to be at least partially be located radially below the first and second plurality of projections 50, 55. The radial distance R5 may be reducible or reduced so that it is smaller than a radial distance R4 that is defined between the longitudinal axis 35 of the tubular body 30 and the free ends 60, 65 of the projections 50, 55 (the free ends 60, 65 are not visible in the cross section shown in FIG. 6b, but they are indicated by crosses in FIG. 6b). This means, that the elongate outer member 75 may be positioned inside the circumference defined by the first and the second plurality of projections 50, 55 so that tissue of the connection channel wall structure 25 is or can be located in the circumferential groove 45 between the groove bottom 46 and the first and second projections 50, 55, wherein the elongate outer member 75 itself may be located inside the groove 45 between the groove bottom 46 and the first and second plurality of projections 50, 55. However, the elongate outer member 75 may also be arranged to force tissue of the connection channel wall structure 25 into the circumferential groove 45 but to remain outside the groove (i.e. R5 may be larger than R4 as it is shown in FIG. 6b). The catheter member 90, or an other, for example similarly structured catheter device, may be used to handle and position the elongate outer member 75 around an exterior of the circumferential connection channel wall structure 25.

Figure 7:
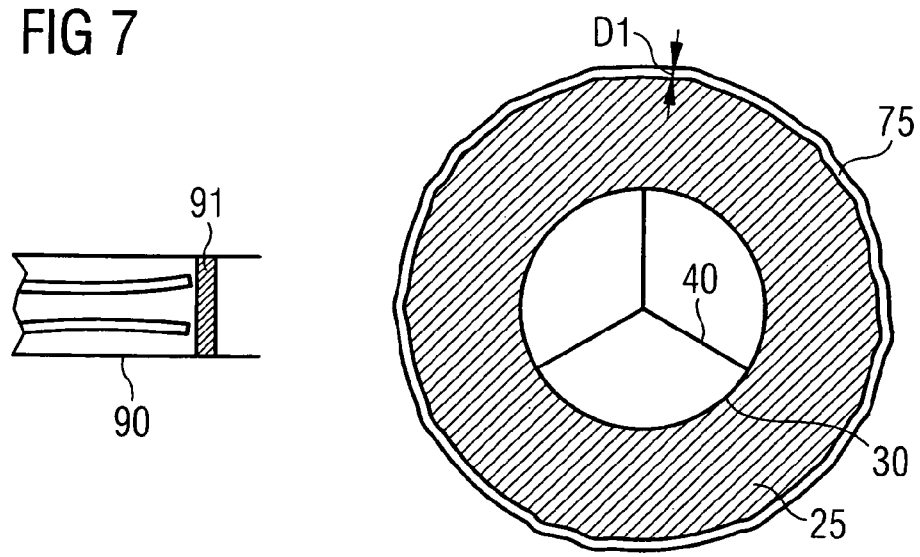
FIG. 7 schematically shows the interaction of a transcatheter valve prosthesis, heart tissue and an elongate outer member according to an embodiment.

With further reference to FIGS. 6b and 7, the catheter member 90 may comprise a connecting means 91, for example a cutting and clamping means, that can be used to connect free ends of the elongate member 75, for example to cut the elongate outer member 75 and clamp two ends of it together, so that the elongate member 75 may remain permanently around the tubular body 30 and thereby forms a component of the prosthesis 1. However, the elongate outer member 75 may also merely be an interventional tool, for example as a component of catheter member, and may only be used to radially force the tissue of the connection channel wall structure 25 into the outer groove 45, and may then be withdrawn or removed from the heart. When the elongate member 75 remains permanently positioned around an outer side of the connection channel wall structure 25, it may permanently apply a radial and inwardly directed force to the tissue of the connection channel wall structure 25 towards the groove 45.

With reference to FIGS. 1, 3, 6b and 7 there may be several ways in which heart tissue of the connection channel wall structure 25 is fixated, held and/or caught in the circumferential groove 45. The tissue may be perforated by the free ends 60, 65 of the first and/or the second plurality of projections 50, 55 e.g. via the acute ends 70 and/or the barbs or hooks 71. The tissue may also be held in the circumferential groove 45 by an interference fit between the projections 50, 55. The tissue may also be held in the circumferential groove 45 by the elongate outer member 75. The elongate outer member 75 may be used to force the tissue into the groove 45 either temporarily (e.g. as a method step during a heart treatment) or permanently (for example, if the cutting and clamping means 91 is used to cut elongate outer member 75 and to connect its two ends together permanently while it is extending around the exterior of the connection channel wall structure 25 as shown in FIG. 7). The tissue of the connection channel wall structure 25 may also be held in the circumferential groove 45 by a combination of two or more of the above described means and effects.

In all embodiments, the elongate outer member 75 may have a cross-sectional diameter D1 (see e.g. FIG. 6b) that is smaller than a width W1 of the outer circumferential groove 45 (illustrated e.g. in FIG. 2). The elongate member 75 may also have a cross-sectional diameter D1 that is smaller than the gap W2 between the free ends 60, 65 of the first and the second plurality of projections 50, 55. The elongate member 75 may have a cross-sectional diameter D1 that is larger than width W2 but smaller than width W1. The elongate member 75 may have a cross-sectional diameter D1 that is larger than width W2 and/or width W1. The elongate member 75 may be a wire or a band, and may have a circular cross section or a rectangular cross section. The elongate member 75 may also have a triangular cross section or a cross section defining any other shape. The elongate member 75 may be made from any material that has been described with reference to the mesh elements 33 or a combination of those materials or other material(s). For example, the elongate member may be made from steel, a titanium alloy or a shape memory alloy such as nitinol.

Further, a length of the projections 50 and/or 55 may be related to the width W1 of the circumferential groove 45. In this respect, the ratio of a distance between the free ends 60, 65 of the first and second pluralities of projections 50, 55 (or, if only one plurality of projections 50, 55 is provided, a distance of the free ends 60, 65 of that plurality of projections 50, 55 to the sidewall 48, 49 of the circumferential groove 45 that is with respect to axis 35 opposite to the projections 50, 55) to the width W1 of the circumferential groove 45 may have a maximum value of 0.5 or 0.4 or 0.3 or 0.2 or 0.1. Accordingly the hollow chamber 66 may be defined between the projections 50, 55 and the groove bottom 46. The width W1 of the circumferential groove 45 may be defined between the sidewalls 48, 49 of the groove 45 and/or between a point from which a projection 50, 55 of the first and/or second plurality of projections 50, 55 extends from the tubular body 30 and a sidewall 48, 49 that is located on an opposite side of the groove (45) and/or between a point from which a projection from the first plurality of projections 50 extends and a point from which a projection form the second plurality of projections 55 extends.

Figure 5:
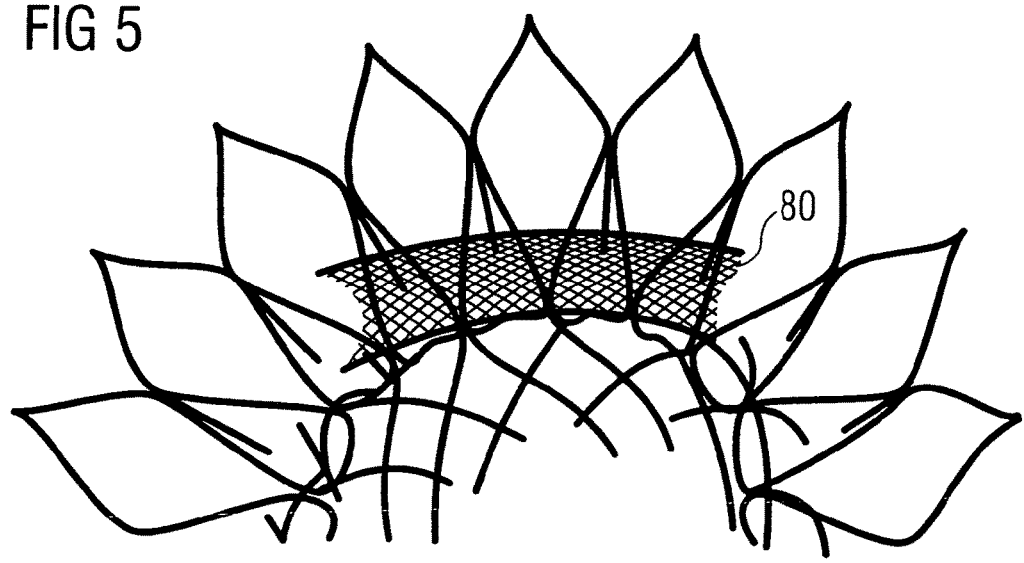
FIG. 5 shows the transcatheter valve prosthesis including the clamping member of FIG. 4 from a different perspective.

With reference to FIGS. 4 and 5 (for improved clarity and understanding, the transcatheter valve prosthesis 1 is shown without artificial valve 40), the transcatheter valve prosthesis 1 may also comprise a clamping member 80. The clamping member 80 may comprise a tubular structure having a longitudinal axis that may be arranged so as to extend in the circumferential groove 45 in a circumferential direction of the tubular body 30. The clamping member 80 may be located in the circumferential groove 45 so as to be located (for example at least partly) radially inwards of the first and second pluralities 50, 55 of projections. The clamping member 80 may be in contact with the groove bottom 46 of the circumferential groove 45. The clamping member 80 may extend around a whole circumference of the tubular body 30 or only partially around the tubular body 30, as shown e.g. in FIGS. 4 and 5. The clamping member 80 may extend e.g. around an angle of 10 to 30 degrees or any other angle in the circumferential groove 45. The clamping member 80 may also extend around the whole circumference of groove 45, e.g. around 360 degrees. The clamping member 80 may have a cross-sectional diameter D2 transverse to its longitudinal axis. The cross-sectional diameter D2 may be selectively changeable to a larger or smaller diameter D2, i.e. the clamping member 80 may be compressible (so as to be insertable via a catheter) and/or expandable (for example, re-expandable after being compressed) in a radial direction of its diameter D2, whereby the inner and outer circumferences of the clamping member are correspondingly decreased/expanded and expanded/decreased, respectively, in a radial direction of the tubular body 30 towards the first and/or the second plurality of projections 50, 55. The cross sectional diameter D2 of the clamping member 80 may be smaller than the cross sectional diameter (radius R1 is shown e.g. in FIG. 6a) of the tubular body 30. The clamping member 80 may be provided in order to clamp heart tissue that is located inside the circumferential groove 45 outwards in a direction from the axis 35 towards the pluralities of projections 50, 55.

Figure 6C:
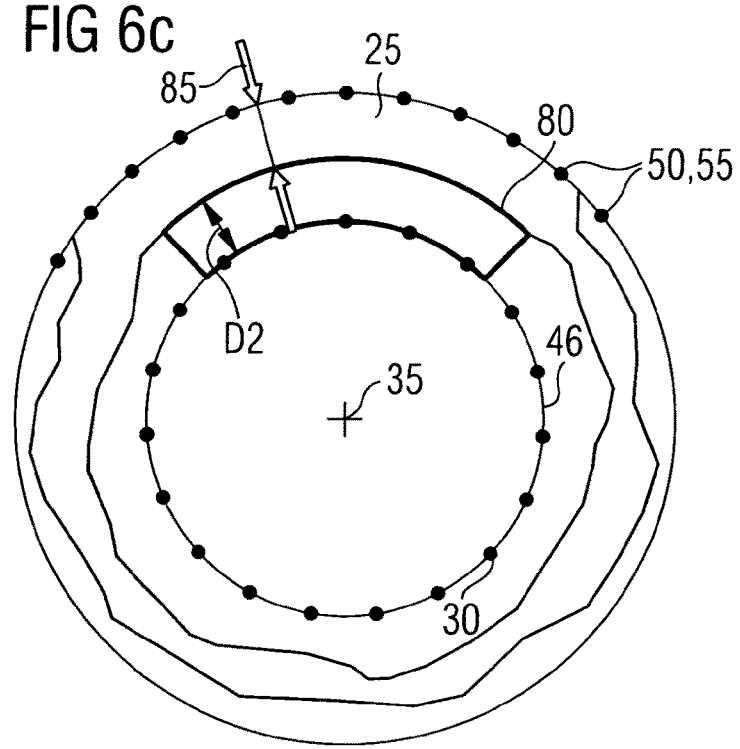
FIG. 6c shows a schematic cross section of a transcatheter valve prosthesis along C-C in FIG. 4 including a clamping member.
Figure 6D:
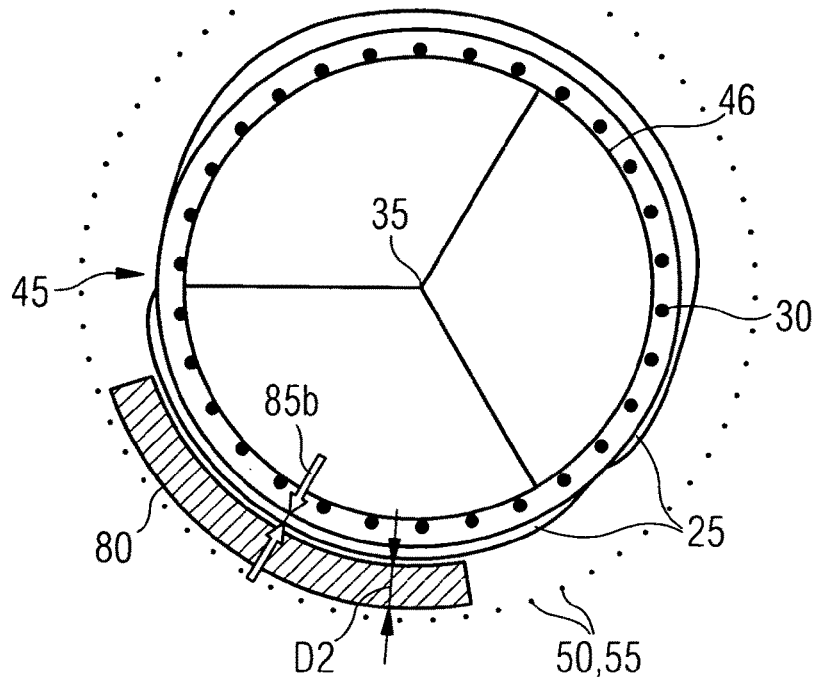
FIG. 6d shows a schematic cross section of a transcatheter valve prosthesis along C-C in FIG. 4 including a clamping member in another arrangement than shown in FIG. 6c.

With reference to FIG. 6d, the clamping member 80 may also be or form part of the above described elongate outer member 75, wherein the clamping member 80 may then be arranged and/or guided and/or positioned (in a radially compressed condition) at the circumferential outer side of the connection channel wall structure 25 to completely or partly extend around the connection channel wall structure 25 at an axial (with respect to the axis 35 of the tubular body 30) level, and may then be radially expanded (in a direction of the diameter D2 of the clamping member 80), whereby its inner diameter in a radial direction of the tubular member 30 then correspondingly decreases to thereby force the tissue of the inwardly arranged connection channel wall structure 25 (which is then arranged inwards of the clamping member 80) radially into the groove 45. That is, the clamping member may be located between the projections 50, 55 and tissue of the connection channel wall structure 25, that may be pressed into the groove 45 by an elastic force exerted by the clamping member 80 on the tissue of the connection channel wall structure 25 and a corresponding reactive force that may be exerted by the clamping member 80 on the projections 50, 55. The forces that may act upon the tissue of the connection channel wall structure 25 exerted by the clamping member 80 and the groove 45 (e.g. the groove bottom 46) are schematically indicated by arrows 85*b*. The elongate outer member 75 and/or the clamping member 80 (which may be the same member) may serve to anchor the prosthesis 1 and to seal the native heart leaflets against the prosthesis 1 against blood flow. Further, immobilization of the native leaflets by the prosthesis 1 as described herein (e.g. comprising a clamping member 80 and/or elongate member 75) may favour the ingrowth of heart (e.g. leaflet) tissue into the prosthesis (e.g. circumferential groove 45) and thereby further improve fixation of the prosthesis 1 relative to the heart and/or sealing against blood flow as the ingrown tissue may additionally or alternatively seal against blood flow on an outside of the tubular body 30.

FIG. 6*c* shows a schematic cross sectional view of the tubular body 30 and the clamping member 80 similar to the cross section CC in FIG. 4, however additionally showing heart tissue of the connection channel wall structure 25 that is not shown in FIG. 4. In FIG. 6*c*, the positions of the first or second pluralities of projections 50, 55 are indicated by dots 50, 55. As can be seen from FIG. 6*c*, the heart tissue of the connection channel wall structure 25 is located inside the circumferential groove 45 radially between the groove bottom 46 of the tubular body 30 and a diameter that is defined by the free ends 60, 65 of the first and/or the second plurality of projections 50, 55. It can be seen from FIG. 6*c* that the clamping member 80 is elastically strained by the tissue of the connection channel wall structure 25 and in turn exerts a force that presses the tissue of the connection channel wall structure 25 against the free ends 60, 65. Arrows 85 indicate the forces that are caused by the clamping member 80 and that act upon the tissue of the connection channel wall structure 25 in the groove 45.

With reference e.g. to FIGS. 6*c* and 6*d*, which show only one clamping member 80, there may also e.g. be two or more clamping members 80 arranged in the groove 45 which are arranged in parallel to each other and/or which are arranged sequentially in a circumferential direction, with for example a circumferential distance therebetween or abutting each other, of the tubular body 30. For example, there may be two clamping members 80 abutting each other and a third clamping member 80 that has an angular distance from the two clamping members 80 that are abutting each other may also be arranged in the groove 45. Clamping members 80 may e.g. be positioned on diametrically opposite sides of the groove 45. These two or more (e.g. 3 to 5) clamping members 80 may all have the same cross-sectional diameter D2 or may each have different cross-sectional diameters. The clamping members 80 may all have the same longitudinal length or may have different longitudinal lengths (e.g. in a circumferential direction of tubular body 30). Clamping members 80 may be designed and arranged so that the tubular body 30 is firmly held in place according to the specific tissue structure and conditions of the connection channel wall structure 25 of a specific heart (e.g. of a patient). They may e.g. be specifically chosen and arranged by an operator or surgeon to firmly hold the tubular body 30 in place according to local conditions. The respective clamping member 80 may have an other shape than a tubular, such as a block-shape, a cubic-shape or a ball-shape.

The force acting on the tissue of the connection channel wall structure 25 may be increased when the clamping member 80 is used together with the elongate outer member 75 thereby further improving the connection between the transcatheter valve prosthesis 1 and the connection channel wall structure 25. In this case, an elastic force origination form the clamping member 80 pointing from the axis 35 outwards and a force originating from the elongate outer member 75 pointing inwards to the axis 35 act upon tissue of the connection channel wall structure 25, thereby holding the prosthesis 1 firmly in its intended position in the connection channel 10. However, the valve prosthesis 1 may be used without the clamping member 80 and the elongate outer member 75 as well (i.e. by itself) or together with only one (anyone) of them. A prosthesis 1 not comprising a plurality of projections 50, 55 may be fixated by clamping member 80 and/or elongate outer member 75, e.g. when the elongate outer member 75 and/or the clamping member 80 are/is generally rigid, e.g. when comprising or being an inflatable balloon that is filled with a substance giving it rigidity caused by a pressure or by a curing of that substance. That substance can cure with a limited amount of time, with the injection of an additional agent (eg a reticulating agent), with application of heat or energy. It can be PMMA (Poly Methyl Methacrylate), different epoxies, polyurethane, a blend of polyurethane silicone. It can be strengthened with the addition of reinforcement fibers (eg Kevlar, carbon).

Clamping member 80 may be made from a mesh-type structure as shown in FIGS. 4 and 5 and may comprise an inner lumen. The mesh may be made from metal or organic material or other material. The mesh of clamping member 80 may be made e.g. from iron, nickel, aluminium and/or titanium and/or alloys of these metals and other elements. The mesh may be made e.g. from steel (e.g. spring steel), and/or an superalloy and/or shape memory alloy (such as e.g. nitinol), Ti 6Al 4V, and/or a precious metal like gold or any combination of those and/or other materials. The mesh of clamping member 80 may also be made from polymers, e.g. from polypropylene or polyvinylchloride, Polyethylene or Nylon. Of course, the mesh may also be made from combinations of these materials, i.e. it may be made from two or more different materials. In one embodiment, the clamping member can be an expandable stent-graft made with a steel or nitinol stent covered with a Dacron or ePTFE graft. The mesh of clamping member may also or additionally comprise any material that has been described with reference to the mesh elements 33 of the tubular body 30 and/or with reference to the elongate member 75 and the clamping member 80 may be designed and a material for it may be chosen so as to create a high elastic force to press the tissue of the connection channel wall structure 25 against the projections 50, 55. Clamping member 80 may also be provided with hooks or barbs to create an attachment to tubular body 30.

Clamping member 80 and/or elongate outer member 75 may also comprise an inflatable inner member (not shown). The inflatable inner member may be disposed in an inner lumen of the clamping member 80 and may be inflated so as to increase diameter D2 of clamping member 80 thereby pressing tissue of the connection channel wall structure 25 against the projections 50, 55 (either from an inner side if the clamping member 80 is arranged in the hollow chamber 66 or from an outer side if the clamping member 80 is initially arranged at an outer side of the connection channel wall structure 25). The inner member may be inflated by the operator using a tubing and fluid from an external pressure source, e.g. a syringe, a fluid bottle or a pump located outside the body. The clamping member 80 may also be an inflatable member 80 that presses tissue of the connection channel wall structure 25 against the projections 55, 55 when inflated. Both the inflatable inner member and the inflatable member 80 may be made from a fluid tight, pressure resistant material, e.g. a material or polymer as described above with reference to the clamping member 80 or any other suitable material. With reference to e.g. FIG. 1I, the inflatable member may comprise an aperture 76 (e.g. a valve, e.g. an opening) through which a substance (e.g. via a delivery tube (not shown)) may be delivered into the inflatable member or out of the inflatable member. The aperture 76 may be selectively permitting the transmission of a substance (i.e. have an "open-state") or may be blocking the transmission of a substance (i.e. have a "closed-state"). The aperture 76 may serve to fill the inflatable member or to un-fill (e.g. to empty) the inflatable member in order to change a cross-sectional diameter of the inflatable member. The clamping member 80 and/or the elongate outer member 75 may be made of an elastic material (e.g. a polymer and/or a metal) and/or may be filled with an compressible (e.g. elastical) substance (e.g. a gas and/or a foam material and/or a hydrogel) to provide a damping/cushioning functionality. A substance for filling the inflatable member may be a gas, a liquid or any other substance and/or may be a substance that changes its phase (e.g. gas, liquid, solid) when in the inflatable member (the substance may e.g. change from liquid phase to a generally solid phase). The substance may be a substance that is capable of curing and/or hardening when disposed in the inflatable member so as to provide a generally rigid clamping member 80 and/or elongate outer member 75.

Clamping member 80 may apply a force to the opposite side walls 48, 49 of groove 45, for instance upon radial expansion relatively to its longitudinal axis. This force may increase or decrease the distance between body sections 31 and 32 and/or the distance between axial ends (with respect to axis 35) of the tubular body 30. Tubular body 30 may be made to be elastic (e.g. comprising a mesh structure and/or an elastic material). The force exerted by clamping member 80 may also result in a expansion or reduction of a perimeter of the groove bottom 46 along a circumference of groove 45 and/or in an expansion or reduction of diameter R1 of the tubular body 30 at an axial height (with respect to axis 35) of groove 45 respectively. The clamping member 80 and/or the elongate outer member 75 (which may be the same member or may be separate members) may also not produce a force in a radial direction and/or a longitudinal direction of the tubular body 30 with respect to its longitudinal axis 35. Accordingly, the clamping member 80 and/or the elongate outer member 75 may act as a displacement member by displacing tissue of the connection channel 10 without exerting a clamping force to the tubular body 30 but by providing a mere interference fit between the circumferential wall structure 25 of the connection channel 10, the clamping member 80 and/or the tubular body 30 in addition or as alternative to e.g. tissue being pierced by projections of the first 50 and/or second plurality of projections 55.

The clamping member 80 and/or elongate outer member 75 may be located only partially radially inwards of the first 50 and/or second 55 plurality of projections and may be located so as to be pierced by anyone or both pluralities of projections so as to be held relative to the tubular body 30. The elongate outer member 75 and/or clamping member 80 may be pierced by only one plurality of projections 50, 55 and the other plurality of projections may not pierce the clamping member 80/elongate outer member 75 (or, the other plurality of projections may not be provided in case of a prosthesis 1 only comprising one (a) plurality of projections (on one side of the groove 45)). The plurality of projections 50 and/or 55 may be piercing the clamping member 80 so that the respective free ends 60, 65 of the projections 50, 55 end inside the clamping member 80 or so that the free ends 60, 65 of the respective projections 50, 55 are penetrating through the clamping member 80 and exit from the clamping member so that the respective free ends 60, 65 may be located outside the clamping member 80.

Figure 10A:
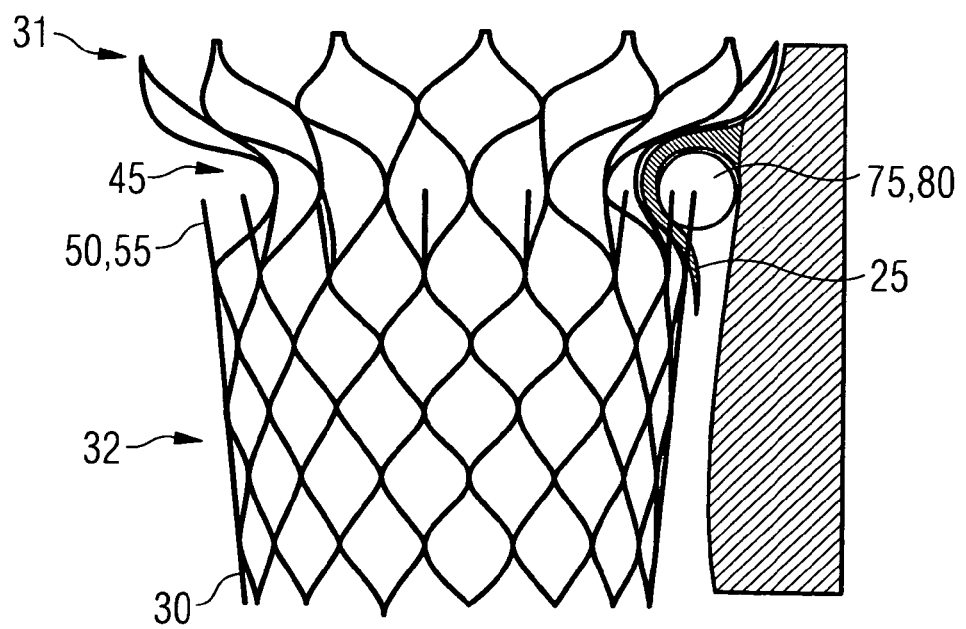
Figure 10B:
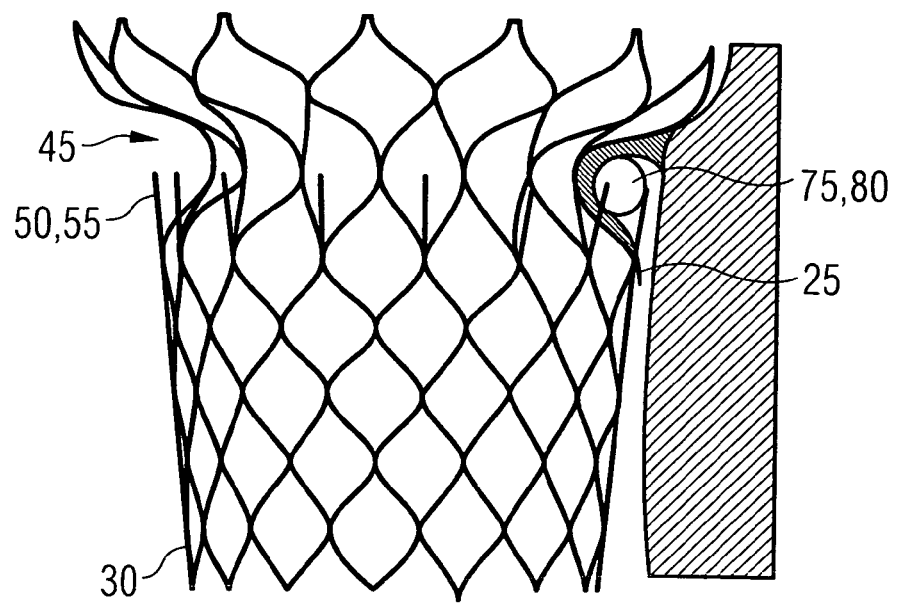

With reference to FIG. 10b, the elongate outer member 75 and/or the clamping member 80 may also be provided in the groove 45 radially inwards of the projections 50, 55 so that the elongate outer member 75 and/or the clamping member 80 is not pierced by the projections 50, 55. The elongate outer member 75/clamping member 80 may be held by a mere interference fit or a frictional/interference fit between the groove 45, the tissue of the connection channel wall structure 25 and/or projections 50, 55 in the groove 45 (e.g. when inflated, e.g. when expanded). Further, as schematically shown in FIG. 10b, the elongate outer member 75/clamping member 80 may have a cross sectional shape that is substantially elliptical or has any other shape, such as a triangular, rectangular or polygonal shape. The substantially elliptical shape of the elongate outer member 75/clamping member 80 that is shown in FIG. 10b may be caused by the design of the elongate outer member 75/clamping member 80, e.g. when it is provided with a tubular structure having a substantially elliptical shape (e.g. when expanded), or it may be caused by anisotropic forces acting upon elongate outer member 75/clamping member 80 caused e.g. by the projections 50, 55, the tissue of the circumferential wall structure 25 and/or groove 45. That is, the elongate outer member 75/clamping member 80 may have a substantially round cross section when no external forces act upon it and may be assuming a different shape (e.g. elliptical), when implanted (and, e.g. expanded).

With reference to e.g. FIG. 10c, an expandable and/or reducible elongate outer member 75 (e.g. clamping member 80) may have a diameter D2 that may be larger than width W1 of circumferential groove 45 when expanded so that the elongate outer member 75 may extend out of the groove 45 and may occupy a space between the circumferential wall structure 25 and tissue forming a heart chamber (e.g. the ventricular chamber 20 and/or atrial chamber 15), i.e. the elongate outer member 75 may form a shape arranged between (e.g. abutting) the connection channel wall structure 25 and tissue/muscles of a heart chamber wall (e.g. of ventricular chamber 20) when expanded (e.g. fully expanded). Accordingly, the elongate outer member 75 may be located (e.g. partially, e.g. a part thereof) radially outside (with respect to axis 35) the circumferential groove 45 and may extend parallel to axis 35 along one or both body sections 31, 32 (e.g. along second body section 32) of tubular body 30 while being (e.g. partially, e.g. a part of elongate outer member 75) located radially outside groove (45). Accordingly, the elongate member 75 may comprise an angularly shaped (e.g. substantially describing an angle of about 90°) cross section with a first angular leg 75a that may be extending with respect to axis 35 generally radially into the groove 45, and a second angular leg 75b that may be extending generally parallel to axis 35 of the tubular body 30 on an outside of the tubular body 30 (e.g. along first body section 31 and/or second body section 32). That is, the elongate outer member 75 (e.g. second angular leg 75b thereof) may be disposed between the first 31 and/or second 32 body section and tissue/muscle forming a wall of a heart chamber such as the ventricular chamber 20 and/or atrial chamber 15. While in FIG. 10a-c the elongate outer member 75/clamping member 80 is only shown on one side of the prosthesis 1, it may also extend fully or partially (as shown e.g. in FIG. 11a-d) around the prosthesis 1 (e.g. the circumferential groove 45). The elongate outer member 75/clamping member 80 may comprise free ends 77, 78 (e.g. two free ends 77, 78) in a direction of a central-longitudinal axis that may be non-connected and/or not abutting each other, i.e. spaced away from each other. The free ends 77, 78 may have an angular distance from each other (e.g. in the groove 45, e.g. when inflated in the groove 45) defined by an angle of e.g. less than 180', less than 90°, less than 45° or less than 10° with respect to axis 35. The aperture 76 may be provided on one of these free ends 77, 78 or a an aperture 76 may be provided on each of the free ends 77, 78. When the elongate outer member 75/clamping member 80 only extends partially around circumferential groove 45 and accordingly comprises free ends, it may have a rigidity caused by a substance, e.g. by a curing substance (that may be cured).

Accordingly, the clamping member 80/elongate outer member 75 (e.g. when it comprises an elastic and/or compressible material, e.g. as described above) may serve to dampen movement of the heart (e.g. caused by the beating heart, e.g. pulse) by acting as a dampening and/or cushioning member between the heart (e.g. a heart chamber) and the prosthesis 1 (e.g. tubular body 30) to further improve the fixation of the prosthesis 1 relative in the heart by reducing forces caused by the beating heart acting on the prosthesis 1 by dampening these forces. Accordingly, the clamping member 80/elongate outer member 75 may absorb movements (e.g. of the ventricular wall (e.g. of the papillary muscle of the ventricular chamber 20) to avoid pulsation of the prosthesis 1. The clamping member 80 may serve to maintain a distance of the prosthesis 1 from tissue of the heart (e.g. from a wall of the ventricular chamber 20 and/or the atrial chamber 15) and thereby improve placement and/or fixation of the prosthesis 1. Accordingly, the elongate outer member 75 and/or the clamping member 80 may serve as a damping member and/or a spacer member. The clamping member 80 and/or the elongate outer member 75 and hence, the groove 45, may be arranged on a side of the ventricular chamber when seen from the annulus of the natural valve having a distance from the annulus.

The shape of a cross section of tubular body 30 across its longitudinal axis (e.g. axis 35) may be modified. Catheter member 90 may comprise or provide a piercing component that can be positioned through the connection channel wall structure 25 (e.g. from an outside of connection channel wall structure 25) and through the tubular body 30 in substantially diametrically positions relatively to an axial (with respect to axis 35) cross section. The piercing component may be hollow and enable placement of an anchor on connection channel wall structure 25 at the distal position of a diameter of the connection channel wall structure 25 relatively to catheter member 90. Said anchor may be attached to a longitudinal end of a longitudinal component (e.g. a tether) which in turn may be provided with a second anchor on its other longitudinal end. The second anchor may be placed by the piercing component upon retrieval of the piercing component form the connection channel wall structure 25 at the proximal end (relatively to catheter member 90) of said diameter on connection channel wall structure 25. The length of said longitudinal component can be designed to be under tension from forces acting on the longitudinal component induced by the first and second anchors, so as to create a deformation of tubular body 30 in a substantially elliptical shape, e.g. the longitudinal component may be shorter than a diameter of the tubular body 30 when no external forces act upon tubular body 30. The longitudinal component may be placed across an inner lumen of tubular body 30 in a position where it does not interfere with the function of valve 40, e.g. be geometrically spaced away from the valve 40. It may also be small enough to avoid significant interference with blood flow through tubular body 30, e.g. may have a radius or a diameter ranging from 100 μm to 1000 μm.

All embodiments of the transcatheter valve prosthesis 1 may comprise positioning and/or orientation devices to facilitate relative and/or absolute positioning of the tubular body 30 and/or the elongate outer member 75 and/or the clamping member 80. These devices may include passive markers that are fixedly attached to the tubular body 30 and/or the elongate outer member 75 and/or the clamping member 80. The passive markers may be made from materials different from the materials of the tubular body 30 and/or the elongate outer member 75 and/or the clamping member 80 in order to improve contrast during medical imaging, e.g. using magnetic resonance or X-ray based imaging techniques. The passive markers may e.g., be made of highly radio-opaque materials thereby allowing to precisely acquire the relative and/or absolute position of the components of the transcatheter valve prosthesis 1 with respect to the body. The passive markers may each have an asymmetrical shape so as to allow identifying the absolute and/or relative position and orientation and thereby the position and orientation of the tubular body 30 and/or the elongate outer member 75 and/or the clamping member 80. The passive markers may also have an identical shape and may be arranged in a certain configuration relative to each other to allow recognition of the orientation. The circumferential groove 45 of the tubular body 30 and/or the tubular body 30 and/or the elongate outer member 75 and/or the clamping member 80 may have passive markers fixedly attached to facilitate positioning them relative to each other using imaging techniques, e.g. passive markers made of highly radio-opaque materials when imaging techniques based on electro-magnetic radiation (e.g. X-ray imaging) are used. In addition and/or as an alternative, the circumferential groove 45 and/or other parts/components of the tubular body 30 and/or the elongate outer member 75 and/or the clamping member 80 may be made from radio-opaque materials.

A method for using a transcatheter prosthesis 1 as described above may comprise:

Placing the transcatheter valve prosthesis 1 within an atrio-ventricular valve, e.g. in a mitral or a tricuspid valve of a human or animal heart, via an insertion catheter. The transcatheter valve prosthesis 1 may e.g. be placed in a connection channel wall structure 25 between a ventricular chamber 20 and an atrial chamber 15 as shown in FIG. 1.

To place transcatheter valve prosthesis 1 within the heart valve, the following approaches may be applied: 1) an arterial retrograde approach entering the heart cavity over the aorta, 2) through a venous access and through a puncture through the inter atrial septum (trans-septal approach), 3) over a puncture through the apex of the heart (trans-apical approach), 4) over a puncture through the atrial wall from outside the heart, 5) arterial access (e.g. the femoral artery through a puncture in the groin) or 6) any other approach known to a skilled person. The approach to the valve is facilitated as the tubular body 30 is radially compressible and extendable and may e.g. be folded and stuffed in a catheter during approach and may be unfolded/extended when being within the circumferential connection channel wall structure 25. The transcatheter valve prosthesis 1 may include the clamping member 80 or the clamping member 80 may be inserted separately via one of the mentioned approaches (e.g. using a catheter) so as to be placed in the circumferential groove 45 of the tubular body 30 when the tubular body 30 is located in the connection channel wall structure 25. The clamping member 80 may be compressible and expandable.

Fixating the transcatheter valve prosthesis 1 in the heart relative to the valve.

For functional replacement of a heart valve, the transcatheter valve prosthesis 1 is fixated relative to the connection channel wall structure 25 and sealed against blood flow on the exterior of the transcatheter valve prosthesis 1 in the connection channel wall structure 25. To achieve this, tissue of the connection channel wall structure 25 adjacent to the circumferential groove 45 may be forced or placed inside the circumferential groove 45 to engage radially below the first 50 and second 55 pluralities of projections whereby the tissue is prevented from slipping out of the groove 45 by the first 50 and/or second 55 plurality of projections, wherein the free ends 60, 65 of the first 50 and/or second plurality 55 of projections may penetrate the tissue. The tissue of the connection channel wall structure 25 may be (completely) perforated, or example partially perforated, by the projections 50, 55 and may thereby be prevented from slipping out of the circumferential groove 45. The clamping member 80 or two or more clamping members 80 may be provided in the circumferential groove 45 to actively press tissue of the connection channel wall structure 25 against the free ends 60,65 so as to interlock the tissue with the free ends 60, 65. This results in the transcatheter valve prosthesis 1 being held in place more firmly and sealed against blood flow between the exterior of the tubular body 30 and the connection channel wall structure 25.

To place tissue in the circumferential groove 45 of the tubular body 30, a method for using a transcatheter valve prosthesis 1 may comprise using an elongate outer member 75 to radially and inwardly force tissue of the connection channel wall structure 25 into the circumferential groove 45 (which may or may not comprise a clamping member 80). With reference to FIG. 3, the elongate outer member 75 may be disposed at an exterior of the connection channel wall structure 25 at a level of the circumferential groove 45. Then, with further reference to FIG. 6b, a distance R5 between the elongate outer member 75 and the axis 35 of the tubular body is reduced (that means that also a distance between the bottom 46 of the circumferential groove 45 of the tubular body 30 and the elongate outer member 75 is reduced) so as to force tissue of the connection channel wall structure 25 into the circumferential groove 45 to fixate the tissue in the circumferential groove 45. The elongate outer member 75 may be handled via a catheter member 90 and an approach as described in relation to the transcatheter valve prosthesis 1 or any other approach may be used in order to bring the elongate outer member 75 in the vicinity of the connection channel wall structure 25. When the tissue of the connection channel wall structure 25 is held in the circumferential groove 45 by the projections 50, 55, the elongated member 75 (and the catheter member 90) may be removed from the heart or, as shown illustratively in FIG. 7, the connecting means 91 of the catheter member 90 may be used in order to permanently connect two (free) ends of the elongate outer member 75 together and cut the ends so that elongate outer member 75 remains permanently on the exterior of a connection channel wall structure 25 on a level of the circumferential groove 45 of the tubular body 30 so as to additionally hold tissue of the connection channel wall structure 25 in the circumferential groove 45.

A method for using the transcatheter atrio-ventricular prosthesis 1 may result in the transcatheter valve prosthesis 1 being fixated to the connection channel wall structure 25 and being firmly held in place via the tissue that is held in the circumferential groove 45 by the free ends 60, 65, optionally supported by the clamping member 80 and/or the permanently disposed elongate outer member 75.

Features of the transcather atrio-venticular valve prosthesis 1 and method steps involving the prosthesis that have been described herein (description and/or figures and/or claims) referring to a transcather atrio-venticular valve prosthesis 1 comprising first 50 and second 55 pluralities of projections also apply to a transcatheter atrio-ventricular valve prosthesis 1 comprising one plurality of projections (50, 55) and vice versa. In particular, features described in the application (description, claims, figures) to further define the projections of the first and second plurality of projections are also applicable to only the first plurality of projections if, for example, the valve prosthesis only comprises the first plurality of projections (as it is, for example, the case in claim 1). All features herein are disclosed to be interchangeable between all embodiments of the transcather atrio-venticular valve prosthesis 1.

The invention claimed is:

1. A system for implanting a heart valve, comprising:
a radially self-expandable tubular body having an inflow end, an outflow end, and a preformed groove (a) disposed in an outer surface of the tubular body between the inflow end and the outflow end, (b) extending at least partially around the tubular body, and (c) having a circumferential opening facially radially outward of the tubular body,
the preformed groove being a depression in the outer surface of the tubular body such that the outer surface of the tubular body curves radially inward, and
the preformed groove being disposed in only a center area of the tubular body;
a valve disposed within and attached to the tubular body; and
a trapping member configured to form at least a partial loop in a circumferential direction around the preformed groove when the tubular body is fully expanded, wherein:
the inflow end of the tubular body is self-expandable to a shape that constrains movement of the tubular body in an outflow direction by contact in a flow direction between the inflow end of the tubular body and an annulus of a native heart valve when the tubular body is deployed within a heart and aligned with the native heart valve, and
the trapping member is configured to extend around portions of chordae and/or leaflets of the native heart valve located within the groove when the tubular body is deployed within the patient and aligned with the native heart valve, and constrain movement of the tubular body in a direction opposite the flow direction.

2. The system according to claim 1, wherein the tubular body is a stent.

3. The system according to claim 1, wherein the trapping member includes a partial loop.

4. The system according to claim 1, wherein the trapping member includes a closed loop.

5. The system according to claim 1, wherein the trapping member and the tubular body are configured to leave a radial gap between (a) at least one of the trapping member and the tubular body and (b) chordae or valve leaflets, when the trapping member is deployed around portions of chordae and leaflets of the native valve within the groove and the tubular body is fully expanded.

6. The system according to claim 1, wherein the trapping member is not configured to apply a radial force inward when deployed.

7. The system according to claim 1, further comprising a projection having a first end located at a side surface of the tubular body and a second free end, the groove defined between the projection and the side surface of the tubular body.

8. The system according to claim 1, wherein an outer diameter of the inflow end is greater than an outer diameter of the outflow end.

9. The system according to claim 1, wherein the preformed groove is disposed in only a center area of the tubular body such that the preformed groove is distal of a proximalmost end of the tubular body and is proximal of a distalmost end of the tubular body.

10. The system according to claim 1, further comprising an elongate outer member configured to extend at least partially around the tubular body to radially force the portions of chordae and/or leaflets into the preformed groove.

\* \* \* \* \*